(12) United States Patent
Woods et al.

(10) Patent No.: US 9,926,612 B2
(45) Date of Patent: Mar. 27, 2018

(54) GLYCAN-SPECIFIC ANALYTICAL TOOLS

(75) Inventors: Robert J. Woods, Athens, GA (US); Loretta Yang, San Diego, CA (US)

(73) Assignees: University of Georgia Research Foundation, Inc., Athens, GA (US); Glycosensors and Diagnostics, LLC, Athens, GA (US)

( * ) Notice: Subject to any disclaimer, the term of this patent is extended or adjusted under 35 U.S.C. 154(b) by 653 days.

(21) Appl. No.: 13/148,289

(22) PCT Filed: Dec. 10, 2009

(86) PCT No.: PCT/US2009/067582
§ 371 (c)(1),
(2), (4) Date: Oct. 28, 2011

(87) PCT Pub. No.: WO2010/068817
PCT Pub. Date: Jun. 17, 2010

(65) Prior Publication Data
US 2012/0040474 A1 Feb. 16, 2012

Related U.S. Application Data

(60) Provisional application No. 61/193,608, filed on Dec. 10, 2008.

(51) Int. Cl.
| | | |
|---|---|---|
| C12N 15/10 | (2006.01) | |
| C12N 9/82 | (2006.01) | |
| C12N 9/24 | (2006.01) | |
| C12N 9/80 | (2006.01) | |

(52) U.S. Cl.
CPC .... *C12Y 302/01018* (2013.01); *C12N 9/2402* (2013.01); *C12N 9/80* (2013.01); *C12N 9/82* (2013.01); *C12N 15/1089* (2013.01); *C12Y 302/01022* (2013.01); *C12Y 302/01023* (2013.01); *C12Y 302/01113* (2013.01); *C12Y 302/01169* (2013.01); *C12Y 305/01026* (2013.01); *C12Y 305/01052* (2013.01)

(58) Field of Classification Search
None
See application file for complete search history.

(56) References Cited

U.S. PATENT DOCUMENTS

| | | | |
|---|---|---|---|
| 5,352,607 | A | 10/1994 | Laine et al. |
| 5,587,292 | A | 12/1996 | Laine et al. |
| 6,090,573 | A | 7/2000 | Laine et al. |
| 6,159,719 | A | 12/2000 | Laine et al. |
| 6,184,027 | B1 | 2/2001 | Laine et al. |
| 6,376,210 | B1 | 4/2002 | Yuan |
| 2004/0229314 | A1 | 11/2004 | Glucksmann et al. |
| 2006/0040327 | A1 | 2/2006 | Amiss et al. |
| 2006/0141480 | A1 | 6/2006 | Ramnarayan et al. |

FOREIGN PATENT DOCUMENTS

| | | |
|---|---|---|
| JP | 2002-503093 A | 1/2002 |
| JP | 2008-507983 A | 3/2008 |
| JP | 2008-518023 A | 5/2008 |
| WO | WO 98/42864 A1 | 10/1998 |
| WO | WO 2006/047639 A2 | 5/2006 |
| WO | WO 2006/093529 A2 | 9/2006 |
| WO | WO 2006/047639 A3 | 4/2007 |
| WO | WO 2007/130453 A2 | 11/2007 |
| WO | WO 2010/068817 A1 | 6/2010 |

OTHER PUBLICATIONS

K.Karaveg et al. "Energetics of Substrate Binding and Catalysis by Class 1 (Glycosylhydrolase Family 47)—Mannosidases Involved in N-Glycan Processing and Endoplasmic Reticulum Quality Control", J. Biol. Chem. 280(33):29837-29848. (Aug. 2005).*
P.S. Chowdhury et al. "Improving antibody affinity by mimicking somatic hypermutation in vitro", Nature Biotechnology 17:568-572 (Jun. 1999).*
A. Rajpal et al. A general method for greatly improving the affinity of antibodies by using combinatorial libraries, PNAS 102(24):8466-8471 (Jun. 2005).*
Aalto et al., "Mutant bacteriophage with non-catalytic endosialidase binds to both bacterial and eukaryotic polysialic acid and can be used as probe for its detection," *Glycoconj. J.* 2001 18:751-758.
Abbott and Pierce, "Lectin-based glycoproteomic techniques for the enrichment and identification of potential biomarkers." 2010 *Meth. Enzymol.* 480:461-476.
Bae et al., "Molecular Basis for the Selectivity and Specificity of Ligand Recognition by the Family 16 Carbohydrate-binding Modules from *Thermoanaerobacterium polysaccharolyticum* ManA." *Journal of Biological Chemistry*. May 2, 2008. 283(18):12415-12425. Available online on Nov. 19, 2007.
Barakat et al., "Exploiting Elements of Transcriptional Machinery to Enhance Protein Stability."*J. Mol. Biol.* 2007. 366:103-116. Available online on Nov. 3, 2006.
Bouckaert et al., "The crystal structures of Man($\alpha$1-3)Man($\alpha$1-O)Me and Man($\alpha$1-6)Man($\alpha$1-O)Me in complex with concanavalin A," *J. Biol. Chem.* Oct. 8, 1999 274:29188-19195.
Bryce et al., "Carbohydrate-protein recognition: molecular dynamics simulations and free energy analysis of oligosaccharide binding to concanavalin A," *Biophys. J.* Sep. 2001. 81:1373-1388.
Chakrabarti et al., "Computational prediction of native protein ligand-binding and enzyme active site sequences," *Proc. Natl. Acad. Sci. USA* Jul. 19, 2005. 102:10153-10158. Available online on Jul. 5, 2005.
Chipot and Kollman, "Alternative Approaches to Potential of Mean Force Calculations: Free Energy Perturbation versus Thermodynamic Integration Case Study of Some Representative Nonpolar Interactions." *J. Comput. Chem.* 1996. 17(9):1112-1131.

(Continued)

*Primary Examiner* — Rebecca E Prouty
(74) *Attorney, Agent, or Firm* — Mueting, Raasch & Gebhardt, P.A.

(57) ABSTRACT

Provided are lectenz molecules, which are mutated carbohydrate processing enzymes that are catalytically inactive and that have had their substrate affinity increased by at least 1.2 fold. Further provided are methods for making and methods of using such lectenz. Additional mutated proteins following the lectenz approach are further provided.

18 Claims, 9 Drawing Sheets

(56) References Cited

OTHER PUBLICATIONS

Clark et al., "Affinity enhancement of an in vivo matured therapeutic antibody using structure-based computational design," *Protein Sci.* May 2006. 15:949-960. Available online on Apr. 5, 2006.

Cummings and Esko, "Principles of Glycan Recognition," in *Essentials of Glycobiology*. 2nd edition. Varki et al., (Eds.) Cold Spring Harbor (NY): Cold Spring Harbor Laboratory Press; 2009. Chapter 27. Available online: <http://www.ncbi.nlm.nih.gov/books/NBK1950/#_ncbi_dlg_citbx_NBK1950>; 16 pages.

DeMarco and Woods, "Structural glycobiology: a game of snakes and ladders," Jun. 2008 *Glycobiology* 18:426-440. Available online on Apr. 4, 2008.

Deng et al., "Selection of antibody single-chain variable fragments with improved carbohydrate binding by phage display" *J. Biol. Chem.* Apr. 1, 1994. 269:9533-9538.

Dennis et al., "Structure and mechanism of a bacterial β-glucosaminidase having O-GlcNAcase activity." *Nat. Struct. Mol. Biol.* Apr. 2006. 13(4):365-71. Available online on Mar. 26, 2006.

Gao et al., "Dynamic O-glycosylation of nuclear and cytosolic proteins: cloning and characterization of a neutral, cytosolic beta-N-acetylglucosaminidase from human brain.". *J. Biol. Chem.* Mar. 30, 2001. 276(13):9838-45. Available online on Jan. 8, 2001.

Garman and Garboczi, "The molecular defect leading to Fabry disease: structure of human α-galactosidase." *J. Mol. Biol.* Mar. 19, 2004. 337(2):319-35.

Haslam et al., "Core fucosylation of honeybee venom phospholipase A2." *Glycobiology* Apr. 1994. 4(2):105-6.

Hastings, "UGA researcher receives NIH award for high-risk, high-reward carbohydrate research; tools will help develop new ways to diagnose and treat host of diseases," UGA Research News Sep. 27, 2010; available online [retrieved on Aug. 19, 2011]. Available on the Internet: <www.ovpr.uga/news/article/20100927-glycan>; 2 pages.

Hayes et al., "Combining computational and experimental screening for rapid optimization of protein properties." *Proc. Natl. Acad. Sci. USA*, Dec. 10, 2002. 99(25):15926-31. Available online on Nov. 21, 2002.

Heikinheimo et al., "The structure of bovine lysosomal α-mannosidase suggests a novel mechanism for low-pH activation." *J. Mol. Biol.* Mar. 28, 2003. 327(3):631-44.

Honegger et al., "Glycosidase Functions in Sperm-Egg Coat Interaction in Ascidians: a Reconsideration and a New Approach." *Ascidian News* [online]. Dec. 2004. No. 56.

Imberty, "Oligosaccharide structure: theory versus experiment," 1997 *Curr Opin. Structural Biol.* 7:617-623.

Jacobson et al., "Three-dimensional structure of β-galactosidase from *E. coli*." *Nature*. Jun. 30, 1994. 369(6483):761-6.

Jokilammi et al., "Construction of antibody mimics from a noncatalytic enzyme-detection of polysialic acid," *J. Immunol. Meth.* 2004 295:149-160. Available online on Nov. 14, 2004.

Kadirvelraj et al., "Understanding the bacterial polysaccharide antigenicity of *Streptococcus agalactiae* versus *Streptococcus pneumoniae*" *Proc. Natl. Acad. Sci. USA* May 23, 2006. 103:8149-5154. Available online on May 16, 2006.

Karaveg, "Energetics of Substrate Binding and Catalysis by Class 1 (Glycosylhydrolase Family 47)—Mannosidases Involved in N-Glycan Processing and Endoplasmic Reticulum Quality Control." *J. Biol. Chem.* Jan. 1, 2005. 280(33):29837-29848. Available online on May 23, 2005.

Karplus and Kushick, "Method for Estimating the Configurational Entropy of Macromolecules." *Macromol.* 1981. 14:325-332.

Kirschner et al., "GLYCAM06: A Generalizable Biomolecular Force Field. Carbohydrates." *J. Comput. Chem.* Mar. 2008. 29(4):622-655. Available online on Sep. 11, 2007.

Kollman et al., "Calculating Structures and Free Energies of Complex Molecules: Combining Molecular Mechanics and Continuum Models." *Acc. Chem. Res.* 2000. 33(12):889-97. Available online on Oct. 4, 2000.

Kortemme and Baker, "A simple physical model for binding energy hot spots in protein—protein complexes," *Proc. Natl. Acad. Sci. USA* Oct. 29, 2002. 99:14116-14121. Available online on Oct. 15, 2002.

Kuhn et al., "Crystal-Structure of Peptide-$N^4$-(N-Acetyl-β-D-Glucosaminyl)asparagine Amidase F at 2.2-Å Resolution." *Biochemistry*. Oct. 4, 1994. 33(39):11699-11706.

Kuhn et al., "Active site and oligosaccharide recognition residues of peptide-$N^4$-(N-acetyl-β-D-glucosaminyl)asparagine amidase F," *J. Biol. Chem.* Dec. 8, 1995. 270:29493-29497.

Lee, "Characterization of a major cluster of nif, fix, and associated genes in a sugarcane endophyte, *Acetobacter diazotrophicus*." *J. Bacteriol.* Dec. 2000. 182(24): 6874-6883.

Lienemann et al., "Toward understanding of carbohydrate binding and substrate specificity of a glycosyl hydrolase 18 family (GH-18) chitinase from *Trichoderma harzianum*." *Glycobiology*. 2009. 19(10):1116-1126. Available online on Jul. 13, 2009.

Mao et al., "Phage-display library selection of high-affinity human single-chain antibodies to tumor-associated carbohydrate antigens sialyl Lewis$^x$ and Lewis$^x$," *Proc. Natl. Acad. Sci. USA* Jun. 8, 1999 96:6953-6958.

McCartney et al., "Glycoside Hydrolase Carbohydrate-Binding Modules as Molecular Probes for the Analysis of Plant Cell Wall Polymers." *Analytical Biochemistry*. Mar. 2004. 326(1): 49-54.

Meier and Duus, "Antibody glycans wiggle and jiggle," Mar. 2011 *Nature Chem. Biol.* 7:131-132.

Mizan et al., "Cloning and characterization of sialidases with 2-6' and 2-3' sialyl lactose specificity from Pasteurella multocida." *J. Bacteriol.* Dec. 2000. 182(24):6874-83.

Moore and Maranas, "Computational challenges in combinatorial library design for protein engineering," *AIChE J*. Feb. 2004. 50:262-272. Available online on Feb. 10, 2004.

Pelkonen et al., "Differential activities of bacteriophage depolymerase on bacterial polysaccharide: binding is essential but degradation is inhibitory in phage infection of K1-defective *Escherichia coli*," *J. Bacteriol.* Dec. 1992 174(23):7757-7761.

Pieper et al., "MODBASE, a database of annotated comparative protein structure models, and associated resources." *Nucleic Acids Res.* Jan. 1, 2004. 32(Database issue):D217-22.

Straatsma, "Holonomic Constraint Contributions to Free Energy Differences from Thermodynamic Integration Molecular Dynamics Simulations." *Chem. Phys. Lett.* Aug. 14, 1992. 196:297-302.

Taroni et al., "Analysis and prediction of carbohydrate binding sites," Prot. Eng. Feb. 2000. 13:89-98.

Tempel et al., "The xenograft antigen bound to *Griffonia simplicifolia* lectin 1-$\beta_4$. X-ray crystal structure of the complex and molecular dynamics characterization of the binding site," *J. Biol. Chem.* Feb. 22, 2002. 277:6615-6621. Available online on Nov. 19, 2001.

Tempel et al., "Structure of Mouse Golgi α-Mannosidase IA Reveals the Molecular Basis for Substrate Specificity among Class J (Family 47 Glycosylhydrolase) α1,2- Mannosidases." *J. Biol. Chem.* Jul. 9, 2004. 279(28):29774-29786. Available online on Apr. 21, 2004.

Tian et al., "Structure-based design of robust glucose biosensors using a *Thermotoga maritima* periplasmic glucose-binding protein," *Protein Sci.* Oct. 2007. 16:2240-2250. Available online on Aug. 31, 2007.

Treynor et al., "Computationally designed libraries of fluorescent proteins evaluated by preservation and diversity of function" *Proc. Natl. Acad. Sci. USA* Jan. 2, 2007. 104:48-53. Available online on Dec. 19, 2006.

Tsui and Case, "Theory and Applications of the Generalized Born Solvation Model in Macromolecular Simulations." *Biopolymers*. 2001. 56:275-291. Available online on Dec. 4, 2001.

United States Trademark "LECTENZ"—Reg. No. 4,264,797; registered on Dec. 12, 2012. Published for opposition on Jul. 7, 2009.

Woods, Robert J, "High-Specificity Affinity Reagents for N-Glycosylation Site Mapping and Glycomics," Grant Abstract, Grant No. GM086991 [online]. National Institute of General Medical Sciences, National Institutes of Health, project dates Sep. 1, 2009 to Aug. 31, 2011 [retrieved on Jan. 15, 2013]. Retrieved from the Internet: <http://projectreporter.nih.gov/pr_Prj_info_desc_dtls.

(56) References Cited

OTHER PUBLICATIONS cfm?aid=7671759&icde=14958299&ddparam=&ddvalue=&ddsub=&cr=1&csb=default&cs=ASC&print=yes>; 2 pgs.
Woods, Robert J, "Oral Candidasis: Antigen Structure and Vaccine Design," Grant Abstract, Grant No. DE013982 [online]. National Institute of Dental & Craniofacial Research, National Institutes of Health, project dates Sep. 29, 2000 to Jul. 31, 2004[retrieved on Jan. 15, 2013]. Retrieved from the Internet: <http://projectreporter.nih.gov/pr_Prj_info_desc_dtls.cfm?aid=6286200&icde=14958427&ddparam=&ddvalue=&ddsub=&cr=10&csb=default&cs=ASC&print=yes>; 2 pgs.
Woods, Robert J, "Computational Analysis of Carbohydrate Antigenicity," Grant Abstract, Grant No. GM055230 [online]. National Institute of General Medical Sciences, National Institutes of Health, project dates Mar. 1, 1997 to Apr. 30, 2007 [retrieved on Jan. 15, 2013]. Retrieved from the Internet: <http://projectreporter.nih.gov/pr_Prj_info_desc_dtls.cfm?aid=6888359&icde=14958503&ddparam=&ddvalue=&ddsub=&cr=25&csb=default&cs=ASC&print=yes>; 2 pgs.
Woods, Robert J, "Integrating Experiment and Theory to Characterize Diagnostic Antibody Specificity," Grant Abstract, Grant No. GM094919 [online]. National Institute of General Medical Sciences, National Institutes of Health, project dates Sep. 1, 2010 to Aug. 31, 2014 [retrieved on Jan. 15, 2013]. Retrieved from the Internet: <http://projectreporter.nih.gov/pr_Prj_info_desc_dtls.cfm?aid=7994664&icde=1495857 3&ddparam=&ddvalue=&ddsub=&cr=11&csb=default&cs=ASC&print=yes>; 2 pgs.
Woods, Robert J, "Conformation of Antigenic Epitopes of C Neoformans Capsular Polysacc: AIDS," Grant Abstract, Grant No. 5P41RR005351-10, Subproject 0041 [online]. National Center for Research Resources, National Institutes of Health, project dates Sep. 30, 1998 to Jul. 31, 1999 [retrieved on Jan. 15, 2013]. Retrieved from the Internet: <http://projectreporter.nih.gov/pr_Prj_info_desc_dtls.cfm?aid=6122208&icde=14958683&ddparam=&ddvalue=&ddsub=&cr=99&csb=default&cs=ASC&print=yes>; 1 pg.
Zacharias et al., "Inversion of Receptor Binding Preferences by Mutagenesis: Free Energy Thermodynamic Integration Studies of Sugar Binding to L-Arabinose Binding Proteins." *Biochemistry*. Jul. 27, 1993. 32:7428-7434.
International Search Report and Written Opinion dated Feb. 23, 2010, in connection with PCT/US2009/067582, filed on Dec. 10, 2009.
International Preliminary Report on Patentability dated Jun. 23, 2011, in connection with PCT/US2009/067582, filed on Dec. 10, 2009.
Barakat et al., "Molecular diversity in engineered protein libraries," *Curr. Opin. Chem. Biol.* Jun. 2007. 11:335-341. Available online on Jun. 4, 2007.
Bradbrook et al., "X-Ray and molecular dynamics studies of concanavalin-A glucoside and mannoside complexes," *J. Chem. Soc. Faraday Trans.* 1998 94:1603-1611.
Brockmann et al., "Selecting for antibody scFv fragments with improved stability using phage display with denaturation under reducing conditions," *J. Immunol. Methods* Jan. 2005. 269:159-170. Available online on Dec. 2, 2004.
Colombo et al., "Towards the understanding of the structure and dynamics of protein-carbohydrate interactions: molecular dynamics studies of the complexes between hevein and oligosaccharidic ligands," *Carbohydr. Res.* Apr. 2, 2004. 339:985-994.
Drickamer, "Engineering galactose-binding activity into a C-type mannose-binding protein" *Nature* Nov. 12, 1992. 360:183-186.
Ducros et al., "Substrate distortion by a β-mannanase: snapshots of the Michaelis and covalent-intermediate complexes suggest a $B^{2,5}$ conformation for the transition state," *Angew. Chem. Int. Ed. Engl.* Aug. 2, 2002. 41:2824-2827.
Feldhaus et al., "Yeast display of antibody fragments: a discovery and characterization platform," *J. Immun. Methods* Jul. 2004. 290:69-80. Available online on May 31, 2004.
Ford et al., "Molecular dynamics simulations of galectin-1-oligosaccharide complexes reveal the molecular basis for ligand diversity" *Proteins* Nov. 1, 2003. 53:229-240. Available online on Sep. 4, 2003.
Hardt and Laine, "Mutation of active site residues in the chitin-binding domain ChBDChiA1 from chitinase A1 of *Bacillus circulans* alters substrate specificity: use of a green fluorescent protein binding assay," *Arch. Biochem. Biophys.* Jun. 15, 2004. 426:286-297. Available online on May 6, 2004.
Huo et al., "Computational alanine scanning of the 1:1 human growth hormone—receptor complex," *J. Comp. Chem.* Jan. 15, 2002. 23:15-27. Available online on Nov. 14, 2001.
Joo Lee et al., "Phage-Display Selection of a Human Single-Chain Fv Antibody Highly Specific for Melanoma and Breast Cancer Cells Using a Chemoenzymatically Synthesized $G_{M3}$—Carbohydrate Antigen,"*J. Am. Chem. Soc.* 2002. 124:12439-12446. Available online on Sep. 28, 2002.
Kraemer-Pecore et al., "Computational protein design," *Curr. Opin. Chem. Biol.* Dec. 2001. 5:690-695.
Kumar and Zewail, "Dynamics of water in biological recognition," *Chem. Rev.* Apr. 2004. 104:2099-2123. Available online on Mar. 27, 2004.
Kumazaki et al., "A novel method for selective isolation of C-terminal peptides from tryptic digests of proteins by immobilized anhydrotrypsin: application to structural analyses of the tail sheath and tube proteins from bacteriophage T4," *Proteins* Sep. 1986. 1:100-107.
Laitinen et al., "Free energy simulations and MM-PBSA analyses on the affinity and specificity of steroid binding to antiestradiol antibody," *Proteins* Apr. 1, 2004. 55:34-43.
Liang et al., "Free Energy Simulation Studies of the Binding Specificity of Mannose-Binding Protein," *J. Phys. Chem.* Feb. 15, 1996 100:2528-2534.
Looger et al., "Computational design of receptor and sensor proteins with novel functions," *Nature* May 8, 2003. 423:185-190.
Masso et al., "Computational mutagenesis studies of protein structure-function correlations," *Proteins* Jul. 1, 2006. 64:234-245. Available online on Apr. 14, 2006.
Moreira et al., "Computational alanine scanning mutagenesis—an improved methodological approach," *J. Comp. Chem.* Feb. 2007. 28:644-654. Available online on Dec. 28, 2006.
Moreira et al., "Unravelling hot spots: a comprehensive computational mutagenesis study," *Theor. Chem. Acc.* Jan. 2007. 117:99-113. Available online on Jul. 11, 2006.
Patrick and Firth, "Strategies and computational tools for improving randomized protein libraries," *Biomol. Eng.* Oct. 2005. 22:105-112.
Pratap et al., "The combination of molecular dynamics with crystallography for elucidating protein-ligand interactions: a case study involving peanut lectin complexes with T-antigen and lactose," *Acta Crystallogr*. Nov. 2001. D57:1584-1594. Available online on Oct. 25, 2001.
Taniguchi and Paulson, "Frontiers in glycomics; bioinformatics and biomarkers in disease," *Proteomics* May 7, 2007. 7:1360-1363. Available online on Apr. 13, 2007.
Voigt et al., "Computationally focusing the directed evolution of proteins," *J. Cell. Biochem Suppl.* 2001. Suppl 37:58-63.
Woods et al., "GLYCAM_93: A generalized parameter set for molecular dynamics simulations of glycoproteins and oligosaccharides. Application to the structure and dynamics of a disaccharide related to oligomannose," in *Complex Carbohydrates in Drug Research*. Bock et al. (Eds.). Munksgaard: Copenhagen, Denmark; copyright 1994. pp. 15-26.
Woods et al., "Molecular Mechanical and Molecular Dynamical Simulations of Glycoproteins and Oligosaccharides. 1. GLYCAM_93 Parameter Development," *J. Phys. Chem.* Mar. 1995. 99:3832-3846.
"Lectenz" [online]. United States Patent and Trademark Office Trademark Electronic Search System (TESS). Trademark application filed on Dec. 26, 2007, and published for opposition on Jul. 7, 2009. Available online [retrieved on Aug. 19, 2011]. Retrieved from the Internet: <tess2.uspto.gov/bin/showfield?f=doc&state=4004:787618.2.1>; 2 pgs.

(56) References Cited

OTHER PUBLICATIONS

"The Research Group of Professor Robert J. Woods," GLYCAM; The University of Georgia | Complex Carbohydrate Research Center: Athens, GA. Available online [retrieved on Aug. 19, 2011]. Retrieved from the Internet: <glycam.ccrc.uga.edu/ccrc/pages/ri.html>; 4 pgs.

"Translational Research: merging computational modeling and protein engineering to design biomolecules," Available online [retrieved on Aug. 19, 2011]. Retrieved from the Internet: <ksamli.myweb.uga.edu/Research.html>; p. 1 of 2.

United States Trademark "LECTENZ"—Reg. No. 4,264,797; registered on Dec. 25, 2012. Published for Opposition on Jul. 7, 2009. Filed Dec. 26, 2007.

Woods, Robert J, "Cryptococcus Neoformans Capsular Polysaccharides Antigenic Epitope Conform: AIDS," Grant Abstract, Grant No. 5P41RR005351-09, Subproject 0041 [online]. National Center for Research Resources, National Institutes of Health, project dates Sep. 30, 1997 to Sep. 29, 1998[retrieved on Sep. 25, 2014]. Retrieved from the Internet: <http://projectreporter.nih.gov/pr_Prj_info_desc_dtls.cfm?aid=6253248&icde=21876699&ddparam=&ddvalue=&ddsub=&cr=100&csb=default&cs=ASC&print=yes>; 1 pg.

Woods, Robert J, "NMR & Molecular Dynamic Studies of Polysaccharides," Grant Abstract, Grant No. 2P41RR005351-16, Subproject 0095 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181442&icde=2187 6699&print=yes>; 1 pg.

Woods, Robert J, "Development of the Amber Force Field," Grant Abstract, Grant No. 2P41RR005351-16, Subproject 0112 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181450&icde=21876699&ddparam=&ddvalue=&ddsub=&cr=70&csb=default&cs=ASC&print=yes>; 1 pg.

Woods, Robert J, "Quantum NMR Methods for Analyzing Glycopeptide Structure & Dynamics," Grant Abstract, Grant No. 2P41RR005351-16, Subproject 0113 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181451&icde=21876699&ddparam=&ddvalue=&ddsub=&cr=71&csb=default&cs=ASC&print=yes>; 1 pg.

Woods, Robert J, "Development of Mesoscale Model Simulating Polysaccharide," Grant Abstract, Grant No. 2P41RR005351-16, Subproject 0114 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181452&icde=21876699&ddparam=&ddvalue=&ddsub=&cr=72&csb=default&cs=ASC&print=yes>; 1 pg.

Woods, Robert J, "Investigation of Ganglioside Responsible for Enterotoxin," Grant Abstract, Grant No. 2P41RR005351-16, Subproject 0115 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181453&icde=21876699&ddparam=&ddvalue=&ddsub=&cr=73&csb=default&cs=ASC&print=yes>; 1 pg.

Woods, Robert J, "Influence of N-Glycosylation on Glycopeptide," Grant Abstract, Grant No. 2P41RR005351-16, Subproject 0116 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181454&icde=21876699&ddparam=&ddvalue=&ddsub=&cr=74&csb=default&cs=ASC&print=yes>; 1 pg.

Woods, Robert J, "Genetic & Computational Analysis of Growth Factor," Grant Abstract, Grant No. 2P41RR005351-16, Subproject 0117 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181455&icde=21876699&ddparam=&ddvalue=&ddsub=&cr=75&csb=default&cs=ASC&print=yes>; 1 pg.

Woods, Robert J, "Modeling the Mechanism of Enzyme Activity," Grant Abstract, Grant No. 2P41RR005351-16, Subproject 0137 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181456&icde=21876699&ddparam=&ddvalue=&ddsub=&cr=76&csb=default&cs=ASC&print=yes>; 1 pg.

Woods, Robert J, "Computational Analysis of Carbohydrate & Protein," Grant Abstract, Grant No. 2P41RR005351-16, Subproject 0140 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181457&icde=21876699&ddparam=&ddvalue=&ddsub=&cr=77&csb=default&cs=ASC&print=yes>; 1 pg.

Woods, Robert J, "Analysis of Relationship Between Anomeric Configuration & Linkage Conformation," Grant Abstract, Grant No. 2P41RR005351-16, Subproject 0144 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info desc_dtls.cfm?aid=7181462&icde=21876699&ddparam=&ddvalue=&ddsub=&cr=78&csb=default&cs=ASC&print=yes>; 1 pg.

Woods, Robert J, "Application of Glycam in Generation of Energy Surfaces," Grant Abstract, Grant No. 2P41RR005351-16, Subproject 0145 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181463&icde=21876699&ddparam=&ddvalue=&ddsub=&cr=79&csb=default&cs=ASC&print=yes>; 1 pg.

Woods, Robert J, "Peptide Mimics of Group B Streptococcal Antigens," Grant Abstract, Grant No. 2P41RR005351-16, Subproject 0146 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181464&icde=21876699&ddparam=&ddvalue=&ddsub=&cr=80&csb=default&cs=ASC&print=yes>; 1 pg.

Woods, Robert J, "Combined Theoretical MD & Experimental NMR Analysis," Grant Abstract, Grant No. 2P41RR005351-16, Subproject 0152 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181465&icde=21876699&ddparam=&ddvalue=&ddsub=&cr=81&csb=default&cs=ASC&print=yes>; 1 pg.

Woods, Robert J, "Synergistic Theoretical & Experimental Approach," Grant Abstract, Grant No. 2P41RR005351-16, Subproject 0153 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181466&icde=21876699&ddparam=&ddvalue=&ddsub=&cr=82&csb=default&cs=ASC&print=yes>; 1 pg.

Woods, Robert J, "Conformational Analysis of Mannosidase Inhibitors," Grant Abstract, Grant No. 2P41RR005351-16, Subproject 0157 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181470&icde=21876699&ddparam=&ddvalue=&ddsub=&cr=83&csb=default&cs=ASC&print=yes>; 1 pg.

(56) References Cited

OTHER PUBLICATIONS

Woods, Robert J, "Carbohydrate Mimicry by Peptide Mimotopes," Grant Abstract, Grant No. 2P41RR005351-16, Subproject 0160 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181477&icde=21876699&ddparam=&ddvalue=&ddsub=&cr=84&csb=default&cs=ASC&print=yes>; 1 pg.

Woods, Robert J, "Glycoprotein Structure /Protein-Carbohydrate Interaction," Grant Abstract, Grant No. 2P41RR005351-16, Subproject 0161 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181478&icde=21876699&ddparam=&ddvalue=&ddsub=&cr=85&csb=default&cs=ASC&print=yes>; 1 pg.

Woods, Robert J, "Selective Inhibition of Golgi Alpha-Mannosidase II," Grant Abstract, Grant No. 2P41RR005351-16, Subproject 0162 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181479&icde=21876699&ddparam=&ddvalue=&ddsub=&cr=86&csb=default&cs=ASC&print=yes>; 1 pg.

Woods, Robert J, "Molecular Modeling," Grant Abstract, Grant No. 2P41RR005351-16, Subproject 0169 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181488&icde=21876699&ddparam=&ddvalue=&ddsub=&cr=87&csb=default&cs=ASC&print=yes>; 1 pg.

Woods, Robert J, "Modeling Transcriptional Pre-Inhibition Complex," Grant Abstract, Grant No. 2P41RR005351-16, Subproject 0180 [online]. National Center for Research Resources, National Institutes of Health, project dates Apr. 4, 2005 to Jan. 31, 2006 [retrieved on Sep. 25, 2014]. Retrieved from the Internet: <http://projectreporter.nih.gov/pr_Prj_info_desc_dtls.cfm?aid=7181499&icde=21876699&ddparam=&ddvalue=&ddsub=&cr=88&csb=default&cs=ASC&print=yes>; 1 pg.

Mega et al., "Conversion of egg-white lysozyme to a lectin-like protein with agglutinating activity analogous to wheat germ agglutinin" *Biochimica et Biophysica Acta*, 1994; 1200(3):331-3.

Parsons et al., "The Identification of Aspartic Acid residue 52 as Being Critical to Lysozyme Activity" *Biochemistry*, 1969; 8(10):4199-205.

Schwarzer et al., "Proteolytic release of the intramolecular chaperone domain confers processivity to endosialidase F." *J. Biol Chem*, Apr. 3, 2009; 284(14):9465-74; published online Feb. 3, 2009.

The Scripps Research Institute (TSRI), "High Throughput Screening (HTS);" 2015. Accessed online on May 18, 2015, via <https://www.scripps.edu/florida/technologies/hts/>, 2 pages.

\* cited by examiner

GLYCAN-SPECIFIC ANALYTICAL TOOLS

This application is the § 371 U.S. National Stage of International Application No. PCT/US2009/067582, filed 10 Dec. 2009, which claims the benefit of U.S. Provisional Application Ser. No. 61/193,608, filed 10 Dec. 2008, each of which are incorporated by reference herein.

STATEMENT REGARDING FEDERALLY-SPONSORED RESEARCH

Part of the work performed during development of this invention utilized U.S. Government funds under R41GM086991 awarded by the National Institutes of Health. Therefore, the U.S. Government has certain rights in this invention.

BACKGROUND OF THE INVENTION

Field of the Invention

The present invention is directed to glycan-specific analytical tools, their methods of use, and processes for making glycan-specific analytical tools. Other analytical tools are further provided herein.

Background Art

Glycans are complex carbohydrates commonly found attached to lipids and proteins. Because of their presence on protein and cell surfaces, complex carbohydrates often occupy a functional position in biological recognition processes. The complex shape, functionality, and dynamic properties of oligo- and polysaccharides allow these molecules to function in intermolecular interactions as encoders of biological information.

Carbohydrate recognition is an integral part of normal biological development, but can also be used by the innate immune system to allow a host organism to identify a foreign pathogen, on the basis of the carbohydrates presented on the surface of the pathogen. Conversely, many bacterial and viral pathogens initially adhere to host tissues by binding specifically to carbohydrates on the host's cell surfaces. Thus, there is an interest in developing therapeutic agents that can interfere with carbohydrate-based host-pathogen interactions or that can function as antibacterial vaccines. Abnormal glycosylation is also a marker for certain types of cancer and other diseases, making them targets for diagnostic and therapeutic applications. For example, the state of modification of intracellular proteins by O-linked N-acetylglucosamine (O-GlcNAcylation) is an important biomarker of changes caused by disease, notably type-2 diabetes mellitus.

Despite the importance of glycans in biological development and disease, there is at present a lack of sufficient glycan-specific analytical tools, which has delayed exploiting aberrant glycosylation in the diagnosis and treatment of disease. For example, a current method for monitoring O-GlcNAc incorporation in cells, and subsequent presentation on proteins, is based on exogenous uptake of labeling reagents, such as N-azidoacetylglucosamine (GlcNAz). Unfortunately, this method is not applicable to the analysis of O-GlcNAc in isolated tissue or protein samples. An alternative O-GlcNAc labeling approach that can be applied in glycomic/proteomic analyses uses chemoenzymatic tagging. A serious limitation of this method is that it also labels other GlcNAc-terminated complex glycans. Thus, there remains a need for analytical tools with defined carbohydrate specificity that can be used to interrogate biological samples in the search for abnormal glycosylation.

Currently, two major types of biomolecules used in glycan-specific analytical applications are sugar-binding proteins (lectins) and antibodies. A major drawback associated with either of these types of reagents is the characteristically weak interactions between carbohydrates and proteins, with dissociation constants typically in the range of milli- to micromolar for lectins and micro- to nanomolar for antibodies. Additionally, a significant difficulty in using antibodies is that carbohydrates are very poor immunogens. They are generally unable to generate a T-cell dependent response and so produce most often IgM class antibodies, which are inconvenient for analytical and diagnostic applications. Single chain chimeras consisting of the variable domains of the heavy and light chains (scFv) can suffer from instability. Additionally, glycan-specific analytical techniques employing antibodies suffer a drawback due to the selectivity of antibodies being context dependent. Alternatively, lectins, with their broad specificity, are limited in their use for analytical applications. Therefore, there exists a need for developing analytical reagents that possess sufficient specificities to the carbohydrate sequence, yet are able to recognize the sequence within a broad range of glycans.

BRIEF SUMMARY OF THE INVENTION

The present invention provides a lectenz comprising a carbohydrate-processing enzyme that has been mutated to eliminate its catalytic activity while maintaining its substrate specificity. In certain embodiments, the lectenz of the present invention has an affinity to glycans that is higher than the $K_m$ of the wild-type enzyme. The lectenz of the present invention may also have a markedly decreased $k_{off}$ rate. In other embodiments, the present invention presents a lectenz comprising a catalytically inactive carbohydrate-processing enzyme, wherein the inactive enzyme comprises one or more amino acid residues that differ from the wild-type residues, said residues are selected from a list consisting of the residues that are proximal to the bound substrate, but which contribute less than about |0.5 kcal/mol| to a gas-phase ($\Delta E_{MM}$) interaction energy, that contribute less than about |0.5 kcal/mol| to a total ($\Delta G$) interaction energy, or any residues that contribute unfavorably to the binding interaction energy, and combinations thereof. Residues that are proximal to the substrate are generally considered here to be within 5 Å of the substrate, but could be farther or closer.

In another aspect, the present invention provides a method for generating a lectenz. In some embodiments, the method comprises: (a) analyzing a sequence of a carbohydrate-processing enzyme for one or more amino acid residues that, when mutated, could affect the affinity of the carbohydrate-processing enzyme to a glycan or the stability of a enzyme-glycan complex; (b) performing a computational simulation to predict binding energies of the enzyme-glycan complex, wherein the carbohydrate-processing enzyme has at least one mutated amino acid identified in step (a); (c) testing carbohydrate-processing enzymes comprising mutations identified in steps (a) and (b) for their ability to form the complex; and (d) identifying mutants from step (c) that exhibit binding affinities to the glycan that are greater than those of WT enzyme.

Another aspect of the present invention provides methods of using lectenz for glycan-specific analytical applications. In certain embodiments, lectenz of the present invention can be used as affinity reagents or as vehicles for tissue staining. In other embodiments, lectenz can be used for enriching a biological sample with a particular glycoform. In yet other embodiments, lectenz find their application for determining specific glycosylation sites on glycoproteins. Other aspects of the present invention involve use of lectenz as vehicles for targeted delivery of active therapeutic agents.

In certain embodiments, the carbohydrate-processing enzyme is a glycosidase enzyme. In other embodiments, the carbohydrate-processing enzyme is a glycosyltransferase enzyme. In other embodiments, the carbohydrate-processing enzyme is a polysaccharide lyase enzyme. In other embodiments, the carbohydrate-processing enzyme is a sulfatase enzyme. In other embodiments, the carbohydrate-processing enzyme is a sulfotransferase enzyme. In other embodiments, the carbohydrate-processing enzyme is a ligase enzyme. In further embodiments, the carbohydrate-processing enzyme is an amidase enzyme. In yet further embodiments, the carbohydrate-processing enzyme is an epimerase enzyme.

Figure 1:
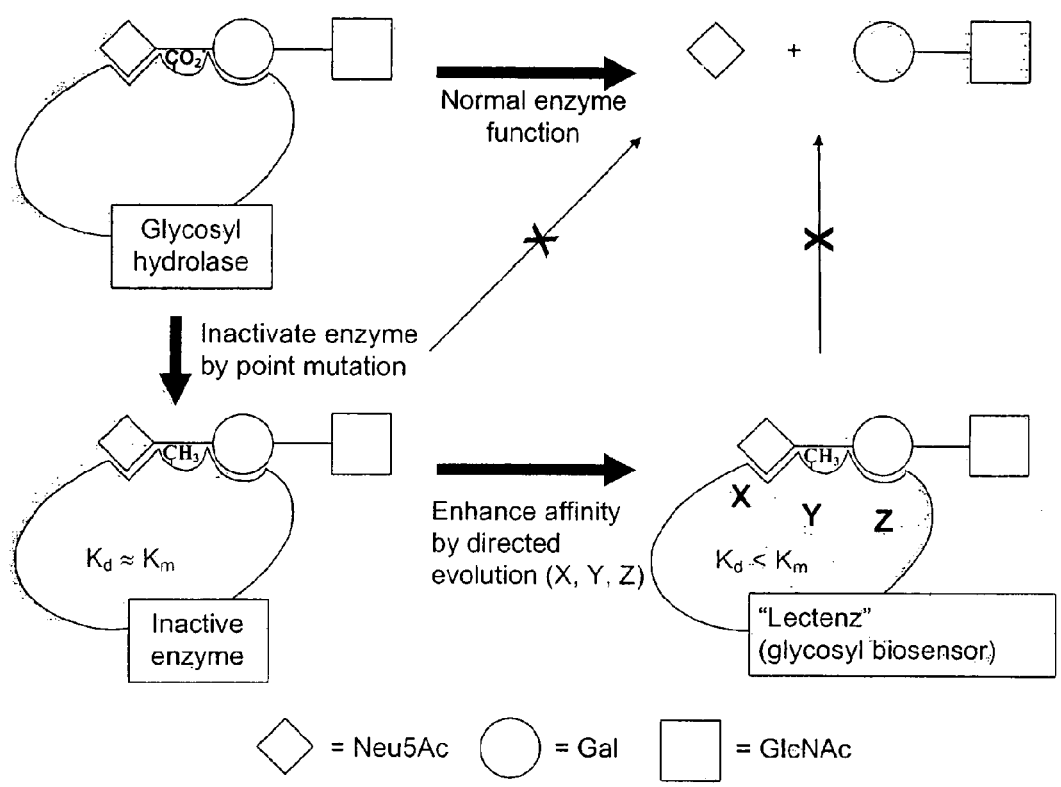
FIG. 1 depicts the relationship between a carbohydrate processing enzyme (a neuraminidase in the example) and its carbohydrate binding lectenz analog.

It is understood that the illustrations and figures of the present application are not necessarily drawn to scale and that these figures and illustrations merely illustrate, but do not limit, the present invention.

DETAILED DESCRIPTION OF THE INVENTION

In the following description, for purposes of explanation, specific numbers, parameters and reagents are set forth in order to provide a thorough understanding of the invention. It will be apparent, however, that the invention may be practiced without these specific details. In some instances, well-known features may be omitted or simplified so as not to obscure the present invention.

The embodiment(s) described, and references in the specification to "one embodiment", "an embodiment", "an example embodiment", etc., indicate that the embodiment(s) described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

I. Definitions

As used herein, a carbohydrate-processing enzyme is a term used to refer to any enzyme that acts on a carbohydrate-containing substrate. Examples include glycosidases, glycosyltransferases, but are not limited to those.

As used herein, the term "glycosidase" is used to refer to an enzyme that catalyzes a hydrolysis of a glycosidic bond. The term "glycosidic bond" refers to a type of a functional group that joins a carbohydrate molecule to another carbohydrate molecule or that joins a carbohydrate molecule to a protein molecule or that joins a carbohydrate molecule to a lipid molecule. The term "carbohydrate" is meant to refer to an organic compound of a general formula $C_m(H_2O)_n$. For the purposes of the present invention, terms "carbohydrate", "complex carbohydrate", and "glycan" are used interchangeably.

The terms "catalytically inactive mutant" or "mutant" or "inactive enzyme" are used interchangeably, and refer to an enzyme that has lost at least 95% of its catalytic activity, and that has an amino acid composition different than the catalytically active enzyme. Stated otherwise, a rate of chemical bond cleavage by the catalytically inactive mutant is, at the most, 5% greater than the rate of the bond cleavage measured under the identical conditions in the absence of any catalyst. By "catalytically active enzyme" it is meant to refer to a protein capable of catalyzing a hydrolysis of a chemical bond. The term "wild-type (WT) enzyme" refers to an enzyme encoded by a gene that has a sequence of a gene as it naturally occurs in an organism, and that has not been altered by human intervention. It is of course understood that a naturally occurring polymorphic form of wild-type enzyme is included within this definition. It is further understood that modifications such as tags or other modifications used in the purification or isolation of a protein that do not otherwise change the natural start or stop codon of a protein fall within the definition of a WT enzyme for purposes of this invention. As used herein, the term "ligand" and "substrate" are used interchangeably, and refer to a molecule to which WT or mutant enzymes can bind.

The lectenz of the present invention have an affinity for the glycan that is higher than the $K_m$ of the wild-type enzyme. To understand the meaning of Km, you need to have a model of enzyme action. The simplest model is the classic model of Michaelis and Menten, which has proven useful with many kinds of enzymes (Equation 1).

$$E + S \underset{k_{-1}}{\overset{k_1}{\rightleftharpoons}} ES \overset{k_2}{\rightarrow} E + P \qquad [1]$$

The substrate (S) binds reversibly to the enzyme (E) in the first reaction. In most cases, you can not measure this step. What you measure is production of product (P), created by the second reaction. The Michaelis and Menten constant (Km) is defined in Equation 2.

$$K_m = \frac{k_2 - k_{-1}}{k_1} \qquad [2]$$

Note that Km is not a binding constant that measures the strength of binding between the enzyme and substrate. Its value includes the affinity of substrate for enzyme, but also the rate at which the substrate bound to the enzyme is converted to product. Only if k2 is much smaller than k−1 will KM equal a binding affinity. It is understood that in the context of a wild-type enzyme that it is difficult to directly measure affinity values, because the WT enzyme is acting on the ligand, for this reason it is convenient to compare the $K_d$ of the inactive enzyme to the $K_m$ of the wild-type enzyme. As used herein, the term "affinity" means a force of attraction between two molecules. Although normally measured relative to the $K_m$ of the WT enzyme, the affinity of the lectenz can also be expressed in terms of a decrease in the dissociation constant, $K_d$ for its ligand relative to an inactive form of the WT enzyme. The dissociation constant, $K_d$, is an equilibrium constant that measures the propensity of a complex to dissociate into its constituents. For a general reaction:

$$iE \rightleftharpoons iE+S \qquad [3]$$

Wherein, iE and S designate inactive enzyme and substrate, respectively, and iES is the inactive-enzyme-substrate complex. The corresponding dissociation constant, $K_d$, is then defined as:

$$K_d = \frac{[iE][S]}{[iES]} \qquad [4]$$

wherein [iE] and [S] designate concentrations of free inactive-enzyme and substrate, respectively, and [iES] is a concentration of the inactive-enzyme-substrate complex. Therefore, in certain embodiments, the increase in affinity of the lectenz is measured by comparing the affinity of the lectenz to a catalytically-inactive form of the WT enzyme that has not been subjected to additional affinity-optimizing mutations. For the purposes of the present invention, the affinity of a protein for its ligand can be expressed in dissociation ($K_d$) or association ($K_a$) constants.

The expression "$\Delta G$" is referred to the Gibbs free energy of binding. The Gibbs free energy is a thermodynamic potential that represents the work which must be done in acting against the forces which hold a complex together, while disassembling the complex into component parts separated by sufficient distance that further separation requires negligible additional work. The expression "$\Delta E_{MM}$" refers to molecular mechanics free energy in gas-phase. Terms "specificity" or "enzyme specificity" are used interchangeably, and refer to an ability of an enzyme to recognize and select ligands containing specific molecular structures from a population of different ligands. The term "non-specific" binding or interaction refers to an event of weak interactions between molecules or residues that is not based on any specific recognition or discrimination of individual molecules or residues.

The term "Molecular Dynamics (MD)" is meant to refer to a form of computer simulation in which atoms and molecules are allowed to interact for a period of time by approximations of known physics, giving a view of the motion of the particles. Classical MD simulations are governed by Newton's equations of motion employing energies and forces derived from a classical force field. A classical force field is a mathematic model that relates the atomic positions in a molecule or aggregate of molecules to the potential energy of the molecule or aggregate. The terms "Ewald treatment" or "Ewald summation", as used herein, describes a method for computing the interaction energies of periodic systems (e.g. crystals), particularly electrostatic energies. By the terms "Verlet algorithm" or "Verlet integration", it is meant a numerical method used to integrate Newton's equations of motion.

II. Lectenz

One aspect of the present invention provides a lectenz. A lectenz of the present invention comprises a catalytically inactive mutant of a carbohydrate-processing enzyme that has substantially the same specificity for a given glycan as the wild-type enzyme, and an increased affinity towards the glycan as compared to the WT enzyme. As used herein, the term "substantially the same" is meant to describe a specificity of the glycosidase mutant that is at least 60% of the wild-type enzyme. In some embodiments, the specificity of the mutant is at least 70% of the WT enzyme. In at least one embodiment, the mutated glycosidase is at least 85% as specific to its substrate as the wild-type enzyme to the same substrate. In other embodiments, the mutated glycosidase is at least 95% as specific to its substrate as the wild-type enzyme to the same substrate.

For an engineered lectenz the mutation of the active site residues offers a route not only to inactivating the enzyme, but potentially to enhancing affinity (FIG. 1). In some embodiments, the affinity of the lectenz towards the glycan is increased from that of the wild-type enzyme. In certain embodiments, the affinity of an lectenz to its substrate can be expressed in terms of a dissociation constant, $K_d$, (See Equations 3 and 4). The smaller the dissociation constant, the more tightly the lectenz is bound to the substrate. In some embodiments of the present invention, the dissociation constant ($K_d$) of the lectenz towards the glycan is at least about 1.2 to about 1,000-fold less than the $K_m$ of the WT carbohydrate-processing enzyme. In other embodiments, the dissociation constant of the lectenz towards the glycan is at least about 2 fold less than the $K_m$ of the WT carbohydrate-processing enzyme. In certain embodiments, the dissociation constant of the lectenz towards the glycan is at least about 10 fold less than the $K_m$ of the WT carbohydrate-processing enzyme. In certain embodiments the dissociation constant of the lectenz towards the glycan is at least about 10,000 fold less than the $K_m$ of the WT carbohydrate-processing enzyme. In further embodiments the dissociation constant of the lectenz towards the glycan is at least about 100,000 fold less than the $K_m$ of the WT carbohydrate-processing enzyme.

It is also understood that the affinity improvement of the lectenz of the present invention can be expressed in terms of a decrease in $K_d$ relative to that of an inactive mutant of the WT enzyme. Thus, the $K_d$ of the lectenz towards the glycan is at least about 1.2 to about 1,000-fold less than that of the inactive WT carbohydrate-processing enzyme. In other embodiments, the dissociation constant of the lectenz towards the glycan is at least about 2 fold less than the $K_d$ of the WT carbohydrate-processing enzyme. In certain embodiments, the dissociation constant of the lectenz towards the glycan is at least about 10 fold less than the $K_d$ of the WT carbohydrate-processing enzyme. In certain embodiments the dissociation constant of the lectenz towards the glycan is at least about 10,000 fold less than the $K_d$ of the WT carbohydrate-processing enzyme. In further embodiments the dissociation constant of the lectenz towards the glycan is at least about 100,000 fold less than the $K_d$ of the WT carbohydrate-processing enzyme.

Lectenz of the present invention are not limited to any specific carbohydrate-processing enzyme. Rather, the present invention is broadly applicable to any glycosidase or glycosyltrasferase enzyme, protein, or polypeptide capable of specifically recognizing a carbohydrate. Examples of glycosidases suitable for the present inventions include, but are not limited to, lactase, amylase, chitinase, sucrase, maltase, neuraminidase, invertase, hyaluronidase, and lysozyme. It is understood that glycosidases categorized by the Enzyme Commission (EC) number 3.2.-.-, wherein "-" is a number, are included in the present invention. Glycosidases of the present invention can be inverting or retaining glycosidases. In one embodiment, the lectenz of the present invention is prepared from PNGase F, isolated from *Flavobacterium meningosepticum*. In another embodiment, the lectenz is prepared from recombinant β-O-GlcNAcase, with the WT sequence as determined for β-O-GlcNAcase isolated from *Bacteroides thetaiotaomicron*. In yet another embodiment, neuraminidase from *Clostridium perfringens* is used to prepare the lectenz. In addition to glycosidases, carbohydrate-processing enzymes suitable for use in the present invention include glycosyltransfeases, including those designated under EC number 2.4.-.-, and polysacharide lyases, including those designated under EC number 4.2.2.-. Other carbohydrate-processing enzymes include carbohydrate esterases, sulfatases, sulfotransferases, or any other enzyme that acts on a carbohydrate substrate. Catalytically inactive carbohydrate-processing enzymes of the present invention can be prepared from carbohydrate-processing enzymes isolated from prokaryotic or eukaryotic organisms, as well as others.

In certain embodiments, the lectenz of the present invention will have high thermal stability. By high thermal stability it is meant that the lectenz retains its tertiary structure at a temperature of at least 40° C. for at least thirty minutes in a physiologically acceptable buffer. A physiologically acceptable buffer generally refers to a 0.01-0.2 M phosphate buffer of pH 6-8, 0-1% NaCl concentration, and 0-20 mM glucose concentration. In certain embodiments, the lectenz remains properly folded at a temperature of at least 60° C. for at least thirty minutes in a physiologically acceptable buffer. In other embodiments, the lectenz retains its tertiary structure at a temperature of at least 80° C. for at least thirty minutes in a physiologically acceptable buffer. If needed, lectenz of the present invention can be prepared from glycosidases isolated from thermophilic or hyperthermophilic organisms. Examples of thermophilic and hyperthermophilic organisms from which carbohydrate-processing enzymes suitable herein can be isolated include, but are not limited to, *Thermus thermophilus, Spirochaeta americana, Pyrococcus furiosus, Methanopyrus kandleri, Pyrolobus fumarii, Geothermobacterium ferrireducens*, and *Archaeoglobus fulgidus*.

In some embodiments, a lectenz of the present invention is characterized by long kinetic off-rates. Kinetic off-rate is measured by a dissociation rate constant ($k_{off}$), or a speed with with a ligand will dissociate from a protein (see Equation 5). Generally, substrate-inactive-enzyme complex formation can be described by the following kinetic mechanism:

$$iE + S \underset{k_{off}}{\overset{k_{on}}{\rightleftharpoons}} iES \qquad [5]$$

wherein iE and S designate inactive-enzyme and substrate, respectively, iES is the inactive-enzyme-substrate complex, and $k_{on}$ and $k_{off}$ are rate constants for complex formation and dissociation, respectively. In at least some embodiments, a lectenz of the present invention will dissociate from its ligand at a rate that is at least about 2-fold slower than that of the WT enzyme. In one embodiment, a rate of a lectenz-glycan complex dissociation is at least 5-fold slower than that of a WT-glycan complex. In yet another embodiment, the rate of dissociation of the lectenz-glycan complex is at least 10-fold slower than that of WT. Comparisons can also be made between the off rate of the lectenz and that of an inactivated WT enzyme. In at least some embodiments, a lectenz of the present invention will dissociate from its ligand at a rate that is at least about 2-fold slower than that of the inactive WT enzyme. In one embodiment, a rate of a lectenz-glycan complex dissociation is at least 5-fold slower than that of a complex between an inactive WT enzyme and a glycan. In yet another embodiment, the rate of dissociation of the lectenz-glycan complex is at least 10-fold slower than that of inactive WT enzyme.

In certain embodiments, the catalytically inactive mutant of the present invention has one or more amino acid residues that differ from the WT residues, and that are selected from residues that are proximal to the substrate in the enzyme-substrate complex, but that contribute more than about −0.5 kcal/mol to total (ΔG) interaction energy, or any residues that contribute unfavorably to the binding interaction energy, and combinations thereof. This set of residues that is close to the substrate, but not forming strong interactions may be termed a tepid set of residues. In certain embodiments, the mutant glycosidase has two or more mutations in the tepid residue set. In other embodiments, the mutant glycosidase has three or more, four or more, or even five or more mutations at these positions.

III. Computer-Aided Methods for Generating a Lectenz

Another aspect of the present invention provides a computer-aided method for generating a lectenz, wherein the lectenz comprises a catalytically inactive mutant of a carbohydrate-processing enzyme, the method comprising:
  (a) analyzing a sequence of a carbohydrate-processing enzyme for one or more amino acid residues that, when mutated, could inactivate the enzyme;
  (b) performing a computational simulation to predict binding energies of the WT enzyme-glycan complex, or of a complex wherein the carbohydrate-processing enzyme has at least one mutated amino acid identified in step (a);
  (c) subdividing the residues on the basis of their predicted interaction energies into two groups, namely, a first group of residues that are essential to defining the specificity of the enzyme, and a second group of residues that are proximal to the substrate but not found to be essential to defining specificity (this second set is referred to herein as tepid residues);
  (d) testing carbohydrate-processing enzymes comprising mutations identified in steps (a), (b) and (c) for their ability to form the enzyme-glycan complex; and (e) identifying mutants from step (d) that exhibit binding affinities to the glycan that are at least 1.2-fold greater than those of WT glycosidase.

Figure 2:
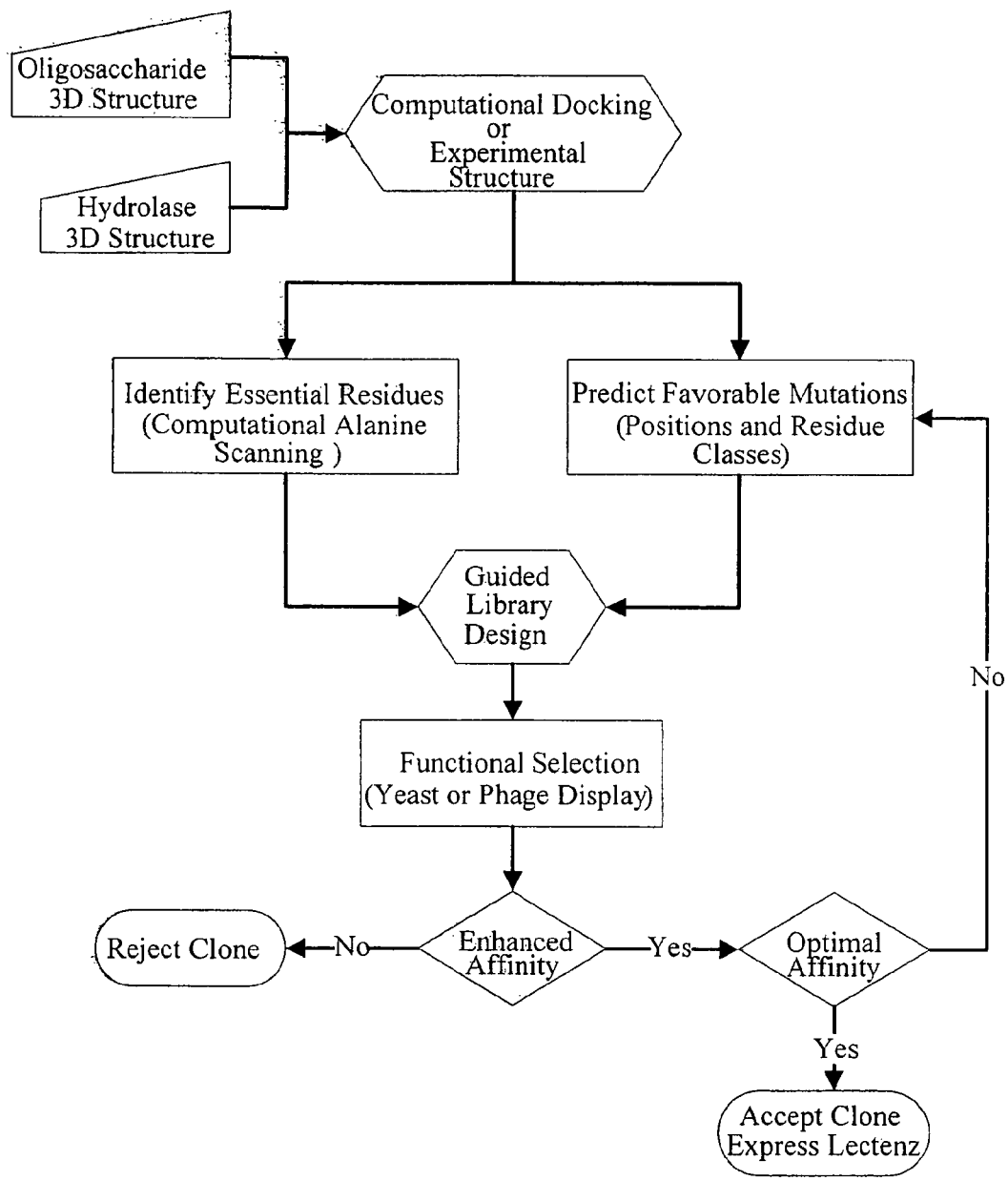
FIG. 2 depicts a protocol combining computational and in vitro display library methods to optimize the affinities of lectenz.
Figure 3:
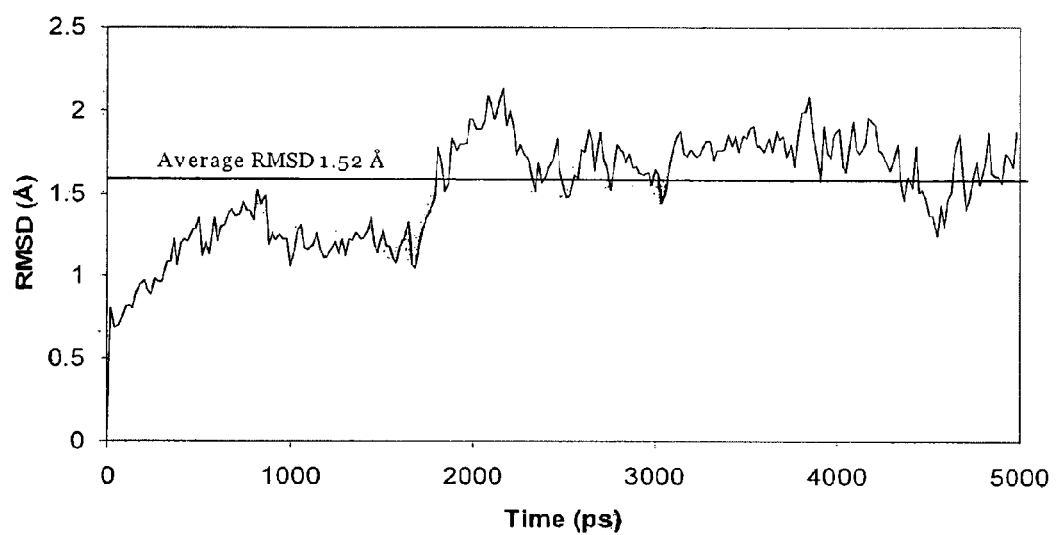
FIG. 3 depicts the RMSD in the Cα positions in the PNGase F complex.
Figure 4:
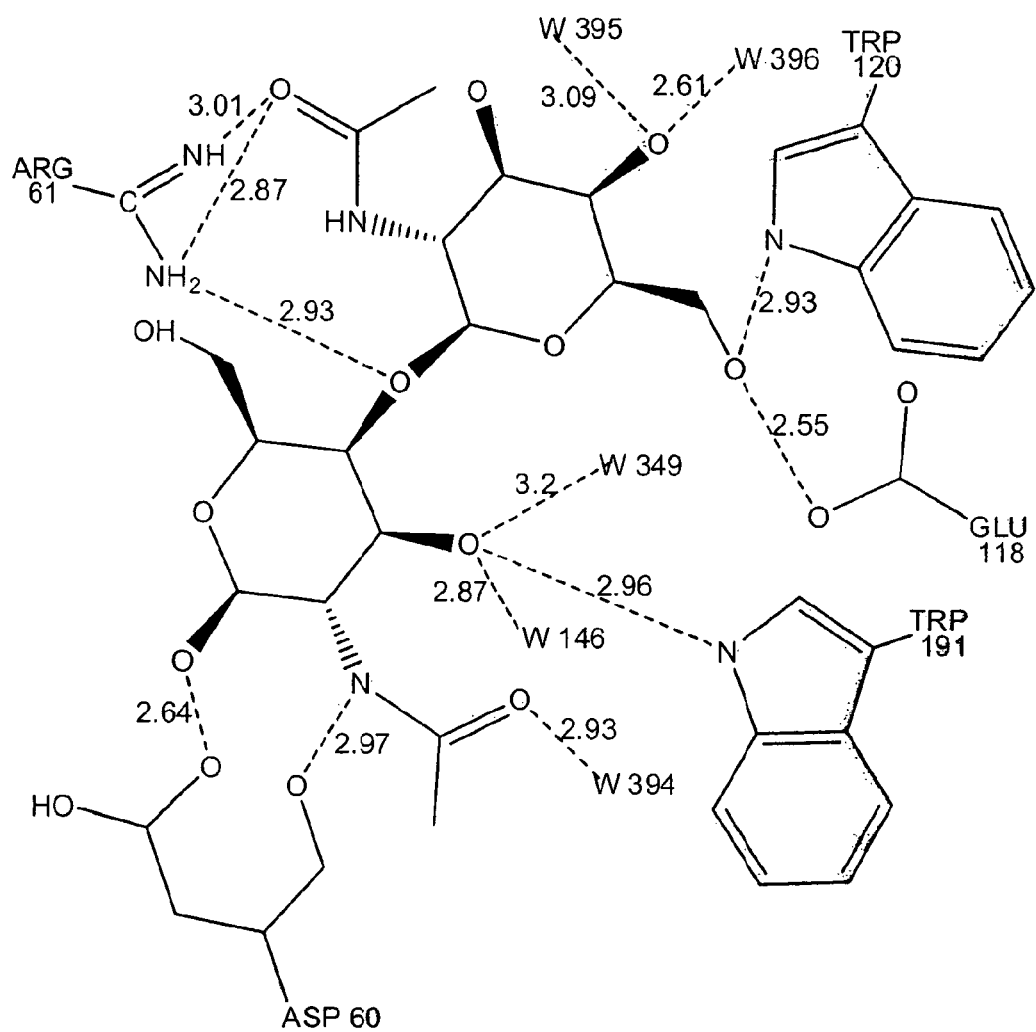
FIG. 4 depicts the hydrogen-bond interaction scheme for the binding of chitobiose to PNGase F.

This embodiment, which is outlined in material form in FIG. 2, is understood to represent only a single embodiment for arriving at the lectenz of the present invention. The steps of FIG. 2, which are described in greater detail herein, can be modified as explained herein to arrive at the lectenz of the present invention. Specifically, for example, to the extent that a particular step in FIG. 2 makes reference to a particular technique, such as "Computational Alanine Scanning" for the "Identify Essential Residues" step, as explained in greater detail elsewhere herein, that is a mere embodiment of the invention and there are other approaches for performing the same step.

Certain embodiments of the present invention involve the identification of carbohydrate-processing enzymes suitable for conversion into a lectenz. While production of a lectenz is not limited to a specific carbohydrate-processing enzyme, it might be preferable to select a carbohydrate-processing enzyme(s) wherein its active site residues are known, and/or for which catalytically inactive mutants have been described. Identification of the catalytic residues has been performed for many carbohydrate-processing enzymes using site-directed mutagenesis and confirmed in many cases by measurements of enzyme kinetics. However, the inactive enzymes (first-generation lectenz) have affinities that are often comparable to lectins.

Generally, before conducting computer-aided mutagenesis techniques, it is preferable to predict the binding affinities of a catalytically inactive carbohydrate-processing enzyme for a ligand of interest. There are a number of well known techniques for characterizing the affinity of a carbohydrate-processing enzyme to its ligand. One such technique is a molecular dynamics (MD) technique that employs the AMBER/GLYCAM protein/carbohydrate force field.

Prior to energy analysis, the root mean squared difference (RMSD) in the positions of the Cα atoms can be determined as a function of the simulation time to determine the stability of the MD simulation and the level of conformational equilibration. On the basis of such data, it can be determined whether the average RMSD was stable and within a range of about 0 Å to 4 Å. It is also possible to discern the time required to reach conformational equilibrium through this approach. It is generally preferable to omit the non-equilibrated portion of the data set in regards to subsequent analyses. In one embodiment, where 5 nanoseconds of data were collected and the system took about a nanosecond to equilibrate, the first nanosecond of data was omitted. It is understood that the 5/1 nanosecond embodiment described above is merely exemplary and is not limiting of the present invention.

Ligand stability in the binding site can be assessed by evaluating intermolecular hydrogen bonds between the glycan and the carbohydrate-processing enzyme. Average values for the hydrogen bonds and their percentage occupancies can be collected, and if possible they are collected along with the crystallographically determined values. By monitoring the RMSD of the position of the ligand in the binding site it is also possible to determine ligand stability in the binding site. Having confirmed that the MD simulation is stable and able to reproduce the experimental interactions between the ligand and the protein, one can then employ that system in subsequent analyses. Typical simulations can be performed under constant pressure and temperature (NPT) conditions or under constant volume and temperature (NVT) conditions. These simulations can be performed with the SANDER module of AMBER and the TIP3P water model. In certain embodiments, protein force field parameters are taken from the Parm99 set and carbohydrate parameters from GLYCAM06. It is also possible to perform the simulations with implicit solvent models under non-periodic boundary conditions.

AMBER is a molecular modeling and simulation package that provides simulation-based methods for structure-based ligand design and understanding of structure and free energy in any complex molecular system. AMBER was developed at and is available from University of California, San Francisco. Other modules within AMBER can be employed to perform these MD simulations. Indeed, programs other than AMBER exist for performing MD simulations. Such programs are also applicable to the present invention.

Under certain embodiments, initial coordinates for the glycan-protein complexes can be selected from crystallographic data from inactive enzyme-substrate, active enzyme-inhibitor, or enzyme-product complexes, if available. A theoretical model for the protein can also be employed, such as a model generated by homology or comparative modeling. When only a structure of the free enzyme is available, a co-complex can be predicted using AutoDock or another equivalent program. AutoDock is a suite of automated docking tools designed to predict how small molecules bind to a receptor of known 3D structure. Other docking programs exist and would be applicable to the present invention.

In certain embodiments, histidine protonation states can be inferred from intramolecular hydrogen bonds where possible, otherwise the histidine can be treated as neutral, protonated at N∈. Any net charge on the complex can be neutralized by the addition of the appropriate number of counter ions ($Cl^-$ or $Na^+$). Typically, the oligosaccharide-protein complexes will be solvated by, for example, ~10,000 TIP3P water molecules, in a periodic cube with a minimum distance between the edge of the box and the closest atom of the solute of 10 Å. Periodic boundary conditions can be applied together with Ewald treatment of long-range electrostatics with a direct space cutoff distance of 12 Å. It is understood that these parameters are not limiting of the invention. Indeed, it is understood that TIP3P is but just one of the classical water models used for computational chemistry. Other water models, such as TIP4P, TIP5P, SPC, BNS, and others, can be used in the present invention. The water can also be approximated using implicit solvation models such as a dielectric constant, a distance-dependent dielectric constant, a generalized Born model, or by the Poisson-Boltzmann approximation.

In certain embodiments, the initial configurations can be energy minimized with the SANDER module. In one embodiment, the initial configurations comprise 5,000 cycles of steepest descent and 25,000 cycles of conjugate gradient energy minimization with the SANDER module. The entire system can then be subjected to simulated annealing by heating followed by cooling. In certain embodiments, the simulated annealing comprises from 5 to 300K in 50 ps, followed by cooling to 5K in another 50 ps. Initial atomic velocities can be assigned from a Boltzmann distribution, generally at 5K. Prior to the production dynamics stage, the entire system can be thermally equilibrated by heating again from 5 to 300K in 150 ps. A 2 fs time step can be used to integrate the equations of motion, using the Verlet algorithm. Bonds containing hydrogen can be constrained to their equilibrium lengths using the SHAKE algorithm. It is understood that these parameters are exemplary only and are not limiting of the invention.

The method of the present invention is not limited to any particular ligand. Ligands suitable for present invention include any natural or synthetic carbohydrate or derivative thereof. Examples of suitable ligands include, but are not limited to, lactose, sucrose, maltose, trehalose, cellobiose, chitobiose, N-linked oligosaccharides, O-linked oligosaccharides, oligosaccharides, monosaccharides, terminal branched and non-branched α-(2,3) and α-(2,6)-Neu5Ac, α-(1-2)-man on high mannose N-glycans, α-Gal on glycoproteins and glycolipids, glycosaminoglycans (such as heparin, heparan, chondroitin, hyaluronic acid and their sulfated analogs), β-N- and β- or α-O-GlcNAc on glycoproteins and glycolipids, β-Gal on glycoproteins and glycolipids, α-1,2/3/6 Man on N-glycans, α-Fuc on N- or O-linked glycans.

A. Computer-Aided Methods for Analyzing Residues that Could Affect Carbohydrate-Processing Enzyme-Glycan Complex Stability Once a carbohydrate-processing enzyme(s) for conversion into a lectenz has been selected, its sequence can be analyzed for amino acid residues that, when mutated, could affect the affinity or stability or specificity of an enzyme-glycan complex.

In some embodiments, the sequence analysis can be performed by computational mutagenesis. In one embodiment, key protein residues affecting protein stability and/or ligand affinity can be identified using computational saturation mutagenesis experiments. The computational saturation mutagenesis is conducted at the amino acid sequence level and involves the replacement of one amino acid side chain by another, followed by computational analysis of the effect of the replacement on the affinity or stability or specificity of the interaction between the substrate and the enzyme. In other embodiments, targeted or random computational mutagenesis can be performed. In other embodiments the contribution made to the stability or the specificity of the enzyme-glycan complex by each amino acid in the enzyme can be computed directly for the glycan-enzyme complex.

In certain embodiments, "hotspots" key protein residues that affect protein stability or ligand affinity or ligand specificity are identified using computational alanine scanning mutagenesis (ASM). ASM can be performed by sequential replacement of individual residues by alanine. ASM can identify residues involved in protein function, stability and shape. Each alanine substitution examines the contribution of an individual amino acid to the functionality of the protein. A general overview of this technique is provided in Kollman, P. A., et al., *Calculating Structures and Free Energies of Complex Molecules: Combining Molecular Mechanics and Continuum Models*. Acc. Chem. Res., 2000. 33(12): p. 889-97 and Arakat, N., et al., *Exploiting Elements of Transcriptional Machinery to Enhance Protein Stability* JMB, 2007. 366(103-116). In a typical example, an MD simulation of the WT enzyme or enzyme-substrate complex is performed and the data collected. Subsequently, the side chains of all (or only selected) residues are truncated to the Cβ position, resulting in their conversion thereby to alanine. Any missing hydrogen atoms are added to form an intact alanine. This procedure is repeated for all of the structures collected in the MD simulation. Once converted to alanine, the effect of the mutation on the stability of the enzyme or the complex can be computed from the MD data. These effects are determined, by monitoring changes in the structure of the complex or protein, or by monitoring changes in the energies associated with the protein or complex. Separate MD simulations can also be performed after the alanine mutation has been introduced. Alanine scanning mutagenesis is not the only scanning mutagenesis method known in the art. Therefore, the discussion of this technique is exemplary only and not limiting of the present invention.

In yet other embodiments, key residues can be identified by the magnitude of their energetic contributions in the wild type complex, or by their proximity to the bound ligand. In one such embodiment, a subset of amino acid residues can be created that comprises identified "hotspot" key residues that directly interact with the substrate through hydrogen-bonds, van der Waals contacts, and/or through water mediated contacts. Any residue that is located no more than about 3.2 Å between non-hydrogen (or heavy) atoms can be considered to directly interact with the substrate through van der walls contacts or through hydrogen-bonds. Any residue that is located no more than about 4.5 Å between non-hydrogen atoms may be considered to interact with the substrate through water mediated contacts or non-specific electrostatic interactions. In other embodiments, the subset will comprise any residue that is identified as contributing less than at least about −0.5 kcal/mol to either the gas-phase ($\Delta E_{MM}$) or total ($\Delta G$) interaction energies.

Alternatively, the hotspots can be subjected to further theoretical analysis to predict either specific favorable mutations or identify classes (neutral, charged, hydrophobic, etc.) of potentially favorable mutations (class-focusing). Hayes, R. J., et al., *Combining computational and experimental screening for rapid optimization of protein properties*. Proc Natl Acad Sci USA, 2002. 99(25): p. 15926-31, describes the class-focusing technique.

In some embodiments, it might be preferred to avoid undue chance of degrading lectenz specificity. In these embodiments, residues that are directly involved in interactions with the substrate will not be initially selected for mutagenesis. In other embodiments, residues that interact non-specifically, but contribute significantly favorably to ligand binding (as identified by interaction energy calculations) will also be excluded from initial mutagenesis studies. All remaining residues, and particularly any that contribute unfavorably to binding, can then be considered for a first round of mutagenesis. In some embodiments, the previously excluded subset members can be subjected to mutagenesis after the initial round experimental and theoretical mutagenesis is complete.

B. Computer-Aided Computational Simulation Methods for Predicting Carbohydrate-Processing Enzyme-Glycan Complex Binding Energies In some embodiments, it will be important to predict the effect of the theoretical mutations performed by any of the computational mutagenesis methods described above on the binding energies of the carbohydrate-processing enzyme-glycan complex. In certain embodiments, the binding energies can be calculated using a free energy perturbation method, also known as thermodynamic integration (TI). TI can be used to quantify the energetic contributions to binding of key structural moieties. Straatsma, *Holonomic Constraint Contributions to Free Energy Differences from Thermodynamic Integration Molecular Dynamics Simulations*. Chem. Phys. Lett., 1992. 196: p. 297-302, Zacharias et al., *Inversion of Receptor Binding Preferences by Mutagenesis: Free Energy Thermodynamic Integration Studies of Sugar Binding to L-Arabinose Binding Proteins*. Biochemistry, 1993. 32: p. 7428-7434, and Chipot and Kollman, *Alternative Approaches to Potential of Mean Force Calculations: Free Energy Perturbation versus Thermodynamic Integration Case Study of Some Representative Nonpolar Interactions*. J Comput Chem, 1996. 17(9): p. 1112-1131, describe the TI methodology. Although TI is generally limited to examining relative binding energies for very similar ligands, it is capable of quantifying the energetic contributions to binding of key structural moieties. In a typical example of a TI simulation, the simulation is performed under modified MD conditions, in which the free energy is computed for the theoretical process of converting the initial residue into the final one through a series of incremental steps, during which the percentage contribution from each state is varied. This non-physical process is performed by mathematically mixing the energy functions for each state and is sometimes referred to as computational alchemy.

In yet other embodiments, the total free energy of binding (ΔG) can be calculated by direct decomposition of the interaction energies between the substrate and the protein (the reactants). Direct ΔG calculations combine molecular mechanics (MM) energy estimates with continuum solvent models, such as Poisson Boltzmann (PB) or generalized Born (GB) that attempt to capture the desolvation free energy. These calculations generally require the additional contributions from conformational entropy to be separately computed.

By way of example, and not by way of limitation, in a typical MM-GB/PB calculation the free energy is computed for the protein ($\Delta G_{protein}$), ligand ($\Delta G_{ligand}$), and complex ($\Delta G_{complex}$) for each structural "snapshot" extracted from the MD trajectories. Depending on the enzyme of interest, the initial portion of the data is discarded to allow the system to equilibrate. For example, in a 5 ns trajectory, the first 1 ns can be discarded. In these models, snapshots of data can be collected at set intervals. By way of illustration only, 2,000 snapshots can selected (at 2 ps intervals) from the remaining 4 ns for molecular mechanical (MM) binding energy analysis. The binding free energy (ΔG) can then be computed by subtraction (see Equation 6). Averaging over the entire trajectory results in the final average interaction energies ($<\Delta G_{bind}>$):

$$<\Delta G> = <\Delta G_{complex}> - <\Delta G_{protein}> - \Delta G_{ligand}>, \quad [6]$$

where the averaging is over the MD snapshots.

The free energies of the components can be computed by separating the energies into three categories, namely molecular mechanical (electrostatic and van der Waals), solvation, and entropic (see Equation 7):

$$<\Delta G> = <\Delta E_{MM}> - T<\Delta S_{MM}> + <\Delta G_{Solvation}> \quad [7]$$

Prior to the analyses, the water molecules can be removed from the solvated trajectories. The energy contribution from solvation can then be obtained through application of the generalized Born (GB) implicit solvation model, which due to its relative speed, is well suited for application to large protein-carbohydrate complexes. The MM-GBSA results compare well with those from the more rigorous MM-PBSA analysis (based on the Poisson-Boltzman implicit solvent approximation). The GB approximation has also been shown recently to work well in computational alanine scanning. In at least one embodiment, the GB method for computing carbohydrate-protein interaction energies employs the GB parameterization of Tsui and Case, *Theory and Applications of the Generalized Born Solvation Model in Macromolecular Simulations*. Biopolymers, 2001. 56: p. 275-291.

In certain embodiments, vibrational, translational, and rotational contributions to the entropy can be derived from a normal mode analysis of the energy-minimized coordinates, while the conformational entropy is estimated from an analysis of the covariance matrix of the relevant internal coordinates. See Karplus and Kushick, *Method for Estimating the Configurational Entropy of Macromolecules*. Macromol., 1981. 14: p. 325-332. In the case of carbohydrates, it is particularly convenient and appropriate to focus on the conformational entropy associated with the inter-glycosidic torsion angles. Changes in conformational entropy, arising primarily from hindered rotations, can be estimated from the motions of the backbone torsion angles in the free and bound forms of each oligosaccharide. From the determinants of the covariance matrices for the torsion angles in the bound and free states the relative conformational entropies can be derived.

In some embodiments, the binding energies are calculated using a classical mechanical force field. Generally, the inter-atomic properties pertinent to the molecules involved are parameterized into the force field. To use the AMBER force field, the values for the parameters of the force field (e.g. force constants, equilibrium bond lengths and angles, charges are inputted). A fairly large number of these parameter sets exist, and are described in detail in the AMBER software user manual. Each parameter set has a name, and provides parameters for certain types of molecules.

In one embodiment, the binding analysis is conducted using GLYCAM/AMBER carbohydrate force field. The GLYCAM06 parameters can be used with a number of biomolecular force fields. Examples of force fields compatible with GLYCAM06 include, but are not limited to, AMBER, CHARMM, NWCHEM, etc. In certain embodiments, the GLYCAM parameters can be augmented by the AMBER parameters for proteins. GLYCAM06 does not employ any default or generic parameters and is no longer limited to any particular class of biomolecules, but is fully extendible in the spirit of a small-molecule force field. GLYCAM06 parameters are described, for example, in Kirschner et al., *GLYCAM06: A Generalizable Biomolecular Force Field. Carbohydrates*. J. Comput. Chem., 2007. Early View (DOI 10.1002/jcc.20820).

In certain additional embodiments, the computational simulation is performed to achieve conformational sampling. Such techniques include molecular dynamics simulation, Monte carlo simulation, or side-chain rotamer searching.

C. Expression and Testing of Carbohydrate-Processing Enzyme Mutants

Upon identification of carbohydrate-processing enzyme mutants with predicted desirable ligand binding characteristics using computational mutagenesis and molecular simulations methods described herein, the affinity and complex stability predictions can be confirmed using experimental mutagenesis. In some embodiments, the coding sequence of a carbohydrate-processing enzyme of interest is amplified from genomic DNA isolated from a suitable species and subcloned into a suitable vector. Routine methods of gene cloning and protein overexpression have been described. The coding sequence from genomic DNA for a carbohydrate-processing enzyme of interest can be isolated from the chosen species and subcloned into any suitable vector. In some embodiments, the vector can be engineered to express a carbohydrate-processing enzyme of interest together with a suitable affinity tag. Tagging of the protein will facilitate its purification using affinity chromatography techniques. In one embodiment, a carbohydrate-processing enzyme can be tagged with a hexahistidine tag. In another embodiment, the carbohydrate-processing enzyme can be engineered to contain an antigen peptide tag. Examples of suitable vectors include, but are not limited to, pOPH6, pET, and pBAD. The pOPH6 can be transformed into the chosen *E. coli* strain for expression. The present invention is not limited to a particular strain of *E. coli* for overexpression of a protein. Examples of suitable strain include DH5α.

Overnight cell culture (5-10 ml) can be inoculated into a suitable amount of nutrient broth (e.g., Luria-Bertani broth) containing adequate amounts of carbon source, minerals, ions, antibiotics, and other reagents. Generally, these batch productions are small scale, i.e., 100-200 ml, but larger volume batches can be prepared. Selection of antibiotics will depend on the engineered resistance of the *E. coli* strain and cloned vector. For example, for a pOPH6 vector cloned into DH5α one might use a Luria-Bertani broth containing 80-120 µg/ml ampicillin, 0.8-1.5% v/v glycerol, 80-150 mM potassium phosphate (pH 7.0), and 0.2-1.5 mM isopropyl β-D-1-thiogalactopyranoside (IPTG). The culture media can be harvested after 4-25 hrs of induction.

In some embodiments, overexpressed enzyme can be isolated. A variety of methods are available for protein purification. In one embodiment, clarified media containing over expressed glycosidase can be passed through an appropriate affinity column. A hexahistidine affinity tagged protein can be purified using a resin immobilized with nickel or cobalt. For example, clarified media can be diluted with cold loading buffer containing an appropriate amount of salt and imidazole, and passed through a Hi-Trap IMAC column (Amersham Pharmacia Biotech) at 2 ml/min. An antigen-tagged protein can be purified by passing it through a resin immobilized with an antigen-specific antibody. The recombinant enzyme can be desalted using an appropriate gel filtration column.

In certain embodiments, experimental mutagenesis is conducted using site-directed mutagenesis according to established protocols. By a way of example, site-directed mutagenesis is performed on the vector comprising the gene for an appropriate glycosidase (e.g., pOPH6) using the QuikChange™ mutagenesis kit from Stratagene (La Jolla, Calif.). The sense and antisense primers for each mutant can be designed based on the sequence of the gene and can be synthesized by an automated DNA synthesizer (Integrated DNA Technologies, Inc.). About 10 to about 20 ng of the plasmid and about 5 to about 20 pmole of sense and antisense primers can be added to the polymerase chain reaction (PCR) mixture, as per manufacturer protocol. PCR can be performed on a thermocycle control unit (MJ Research, Cambridge, Mass.). The DNA template can be digested by the addition of an appropriate endonuclease, as per manufacturer protocol. In some embodiments, the full coding region of each mutant will be fully sequenced to confirm that only the desired mutation is generated. In some embodiments, confirmed mutant DNAs can be used as a template to create the multiple mutations by the same procedure as used in the single amino acid mutation.

Once amino acids are mutants identified via computational methods for saturation mutagenesis, a library of mutant proteins can be screened for mutants for desirable binding characteristics. A number of technologies used for high throughput screening of protein-ligand interactions are available in the art. Examples of such technologies suitable for the present invention include, but are not limited to, two-hybrid system, mRNA display, phage display, yeast display, ribosome display, and bacterial display. The approach of the present invention provides an additional subjective way to identify sites in the protein that should be randomized in the library. Thus, by combining the computational analysis of the present invention, one is able to design and then construct a focused biocombinatorial library. Such libraries by their design and construction provide a far more efficient approach for library screening.

In some embodiments, high throughput screening of protein-ligand interactions can be performed by creating a mutagenic display library. One such library system can be synthesized by GENEART. In one embodiment, the library can be displayed on a phage. The phage display library can be constructed using protocols well-established in the art. By way of example, the DNA library encoding the protein or peptide of interest is ligated into the pIII or pVIII gene of M13 filamentous phage. The phage gene and insert DNA hybrid is then transformed into *E. coli* bacterial cells such as TG1 or XL1-Blue *E. coli*. If a "phagemid" vector is used (a simplified display construct vector) phage particles will not be released from the *E. coli* cells until they are infected with helper phage, which enables packaging of the phage DNA and assembly of the mature virions with the relevant protein fragment as part of their outer coat on either the minor (pIII) or major (pVIII) coat protein. The incorporation of many different DNA fragments into the pIII or pVIII genes generates a library from which members of interest can be isolated. By immobilizing a relevant DNA or protein target(s) to the surface of a well, a phage that displays a protein that binds to one of those targets on its surface will remain while others are removed by washing. Those that remain can be eluted, used to produce more phage (by bacterial infection with helper phage) and so produce a phage mixture that is enriched with relevant (i.e. binding) phage. The repeated cycling of these steps is referred to as 'panning', in reference to the enrichment of a sample of gold by removing undesirable materials.

Figure 7:
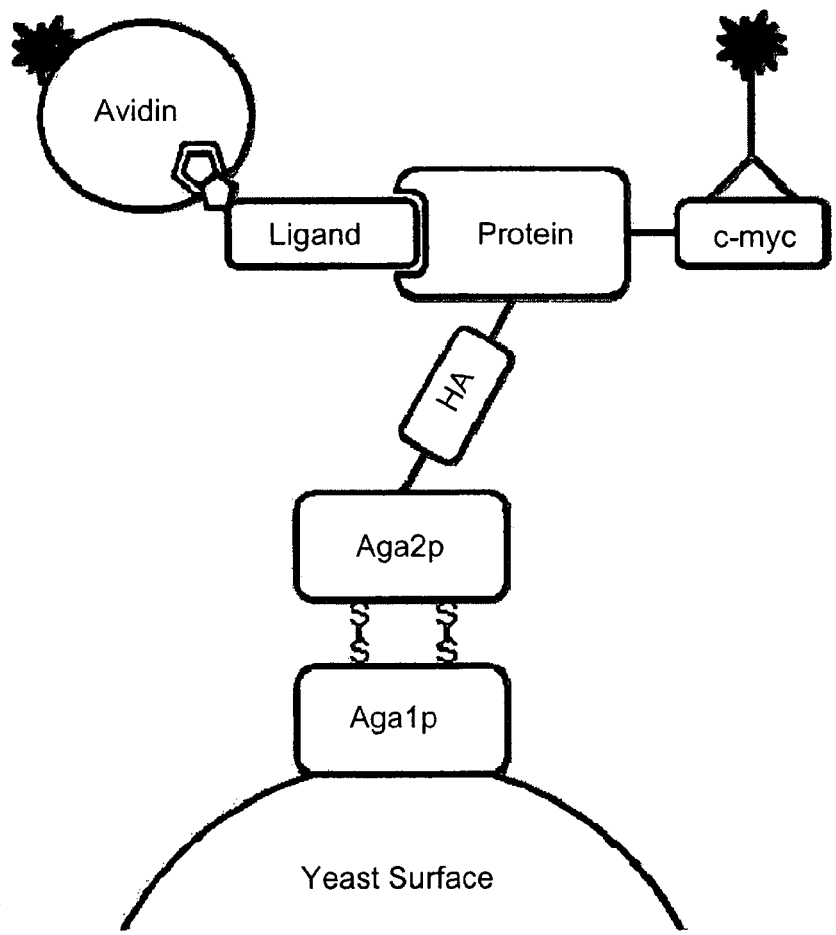
FIG. 7 depicts a protein display library fused to the Aga2 protein in yeast. Detection of a fluorescently labeled antigen binding to c-myc tagged protein is illustrated.

In other embodiments, the mutagenic display library can be displayed on yeast. In yeast display, a protein of interest can be displayed as a fusion to the Aga2p protein on the surface of yeast. The Aga2p protein is naturally used by yeast to mediate cell-cell contacts during yeast cell mating. As such, display of a protein via Aga2p projects the protein away from the cell surface, minimizing potential interactions with other molecules on the yeast cell wall. See FIG. 7, which illustrates the expression vector as a fusion of the Aga2 gene, a HA (hemagglutinin) tag, the displayed protein, and the c-myc tag. A yeast display library can be constructed using protocols well-established in the art. In some embodiments, the gene of interest can be cloned into a vector of choice in frame with the AGA2 gene. Examples of suitable vectors include, but are not limited to, pYD1 vector (Invitrogen) and pPNL6 (Pacific Northwest National Laboratory). The resulting construct is then transformed into suitable yeast strain (e.g., EBY100 *S. cerevisiae*) containing a chromosomal integrant of the AGA1 gene. Expression of both the Aga2 fusion protein from the vector and the Aga1 protein in the EBY100 host strain is regulated by the GAL1 promoter, a tightly regulated promoter that does not allow any detectable cloned protein expression in absence of galactose. Upon induction with galactose, the Aga1 protein and the Aga2 fusion protein associate within the secretory pathway, and the cloned mutant is displayed on the cell surface.

Once a mutagenic library displaying mutated carbohydrate-processing enzymes on cell surfaces is constructed, it can be screened to identify mutants that have desirable binding and complex-formation properties. The basic principle of the assay system used to identify mutants that are capable of high-affinity complex formation with a ligand of choice involves preparing a reaction mixture containing the display library and the ligand under conditions and for a time sufficient to allow the two reagents to interact and bind, thus forming a complex. The formation of any complexes between the binding partners is then captured. After the reaction is complete, unreacted components are removed (e.g., by washing) and any complexes formed will remain immobilized on the cell surfaces. The detection of complexes anchored on the cell surface can be accomplished in a number of ways. In some embodiment, the ligand can be pre-labeled, either directly or indirectly. Where the ligand is labeled, the detection of label immobilized on the cell surface indicates that complexes were formed. Where the binding partner is not pre-labeled, an indirect label can be used to detect complexes anchored on the surface. Labeling of molecules is well known, for example, a large number of biotinylation agents are known, including amine-reactive and thiol-reactive agents, for the biotinylation of proteins, nucleic acids, carbohydrates, carboxylic acids. A biotinylated substrate can be attached to a biotinylated component via avidin or streptavidin.

In some embodiments, the size of the display library can be enriched to comprise yeast that bind biotinylated N-linked glycopeptides with low to high affinity. Low affinity interactions are difficult to measure directly. By immobilizing biotinylated N-linked glycopeptides to the surface of streptavidin coated paramagnetic beads (e.g., Invitrogen), the library can be enriched for yeast displaying proteins that binds to the target on the bead surface. The yeast captured by the N-linked glycopeptide coated paramagnetic beads are isolated with a magnet, nonbinding yeast washed away, and the panning process repeated. In some embodiments, the library can be reduced to $10^6$-$10^8$ cells depending on the initial size of the library and number of rounds of panning. In at least one embodiment, the library is reduced to about $1 \times 10^7$.

Figure 8:
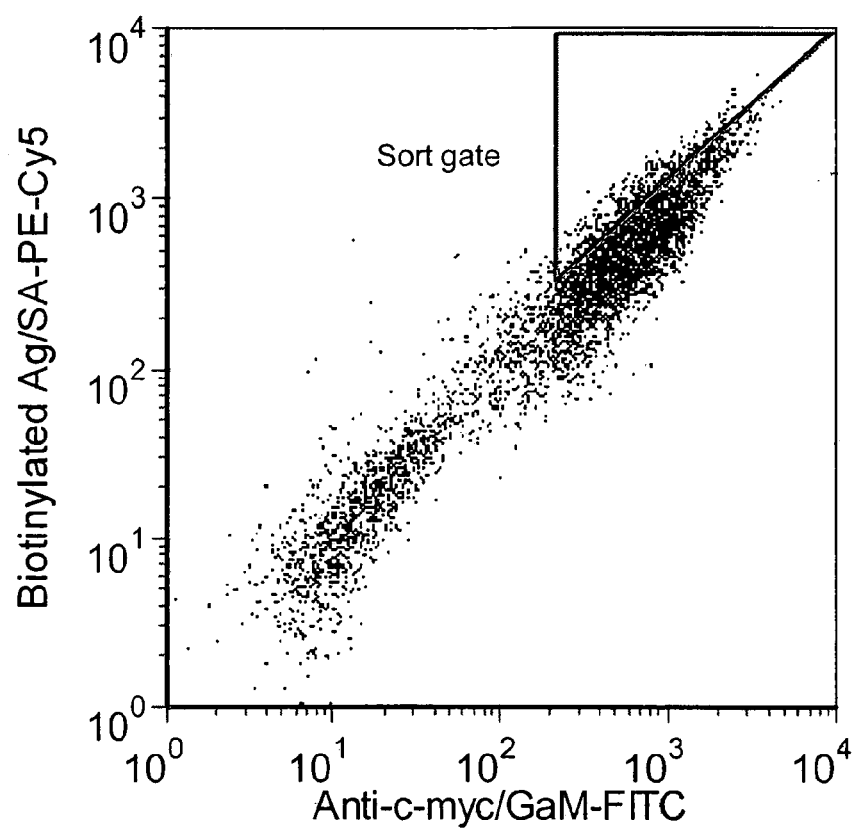
FIG. 8 depicts a cell sorting via flow cytometry indicating the selection of high affinity clones.
Figure 9:
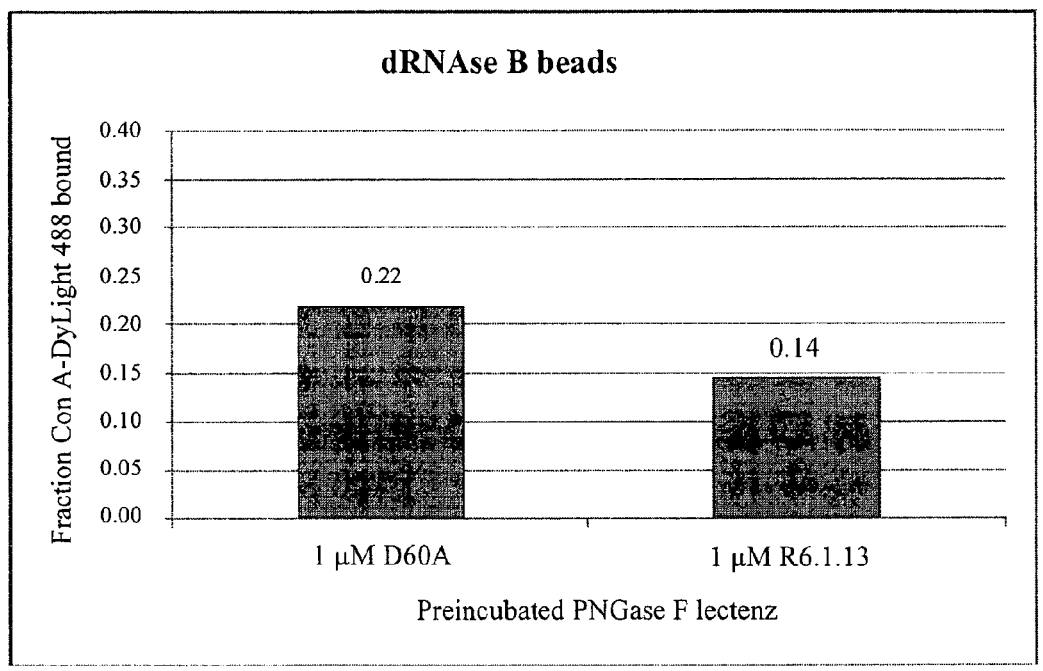
FIG. 9 depicts the enhanced affinity of a preliminary lectenz relative to the inactive enzyme.

In certain embodiment, an initial screening of high-affinity mutants can be conducted. In these embodiments, the screening can be done by flow cytometry. The screening can be done by selecting only the mutants that bind to specific biotinylated glycopeptides. By a way of example, and as detailed in FIG. 9, the yeast expressing the Aga2p fusion protein with a C-terminal c-myc tag can be incubated with anti-c-myc mAb, followed by an addition of a fluorescent secondary mAb to detect the yeast that have expressed full-length glycosidase clones. In certain embodiments, detection of mutants that bind to the biotinylated glycopeptides can be accomplished by addition of streptavidin. In one embodiment, streptavidin can be labeled with a suitable fluorescent label (e.g., PE-Cy5). Streptavidin-PE-Cy5 can be used to fluorescently label the enzyme clones that bind the glycopeptides. Only the cells expressing c-myc that have a high affinity for the glycopeptides will be sorted (FIG. 8). In some embodiment, the dissociation constants of selected glycosidase mutants displayed on individual yeast clones can be determined. In at least one embodiment, the dissociation constant can be determined by flow cytometry.

In certain embodiments, high affinity binders identified in the preliminary screening assay can be expressed and purified for further binding studies. Binding affinities of generated lectenz can be analyzed by a variety techniques known in the art (e.g., filter binding assay, electrophoretic mobility shift assay (EMSA), surface plasmon resonance (SPR), etc.). In one embodiment, binding constants are measured by SPR using a Biacore apparatus. A typical assay used to evaluate binding constants of a complex using SPR includes immobilization of a lectenz of interest on an SPR chip surfaces at 20-30° C. by a suitable coupling method (e.g., amine-coupling method), with mock-derivatized flow cells serving as reference surfaces. The binding analyses can be performed at various temperatures with continuous flow (10-50 µl/min) of running buffer. The running buffer can be 15-25 mM Tris-HCl (pH 7.5), 100-200 mM NaCl, 0.5-1.5 mM EDTA, 0.0025-0.0075% P20 detergent. Ligands can be prepared by serial dilution in the respective running buffers in to obtain an appropriate concentration range. The binding of ligand can be analyzed in a concentration series (0.625-10 µM) over a low-density immobilization surface of lectenz. The maximal equilibrium sensogram values can be used to plot a saturation binding curve and calculate values for the equilibrium dissociation constant ($K_d$) directly.

In one aspect of the present invention, the method for generating lectenz further comprises using crystallographic data for enzyme-substrate or enzyme inhibitor complexes as the basis for computational mutagenesis. In general, crystallization and crystal growth parameter optimization of the lectenz with substrates can be performed by the methods and procedures described in the art. Conditions suitable for crystallization will be determined on a case-by-case basis. Crystals can be tested for diffraction and the crystals which diffract to the highest resolution can be used for data collection. In certain embodiments, Molecular Replacement will be used to solve the structure of the complexes. In these embodiments, X-ray data of generated lectenz-glycan complexes can be used to validate the MD simulations and/or to initiate new simulations.

Although exemplified throughout the present invention in terms of a lectenz derived from a glycan processing enzyme, it is understood that the present invention is broadly applicable to any enzyme-substrate complex. Thus, without being limited to the following examples, and simply to further exemplify the scope of the present invention, the lectenz approach can be used to convert enzymes such as proteases, lipases, kineases, phosphatases, hydrolases, isomerases, and others, to receptor proteins maintaining specificity for the enzyme substrate.

Moreover, the present invention is not limited to carbohydrate processing enzymes. It is further applicable to carbohydrate binding proteins. Indeed, it is applicable to protein-ligand interactions in general.

V. Methods of Use

Another aspect of the present invention provides methods of using lectenz described herein. The vast number of potential applications of lectenz described herein will be immediately apparent to persons skilled in the art. Below are but a few embodiments describing potential utilities of such reagents.

In certain embodiments, lectenz of the present invention can be used for application in glycan-specific analytical tools. Lectenz-based glycan-specific analytical tools of the present invention have potential use as a method of detection in many areas, including environmental, fermentation, food and medical areas and could be used for in vivo or in vitro sensing in humans or animals.

In some embodiments, lectenz with defined carbohydrate specificity described herein can be used to interrogate biological samples in the search for abnormal glycosylation. Examples of biological samples include, but are not limited to, any biological fluid, tissue, or organ. Examples of the biological fluids include, but are not limited to blood, urine, serum, saliva, cerebra-spinal fluid, and semen. In other embodiments, lectenz of the present invention can be used for a detection of a target carbohydrate-based analyte level in biological fluids. Examples of the target analytes include, but are not limited to, endogenously found molecules, such as N- or O-linked glycans, glycosaminoglycans (including heparin), exogenously consumed species, such as plant polysaccharides, carbohydrate-based drugs, and pathogens, whose surfaces are often coated in complex distinct glycans. In other embodiments, the lectenz described herein find their application in drug discovery and evaluation of biological activity of new glycan-based compounds.

In some specific embodiments, lectenz described herein can be used for diagnosing, and/or treating diseases manifested by abnormal glycosylation. In one embodiment, lectenz of the present invention can be used to detect certain tumor antigens comprising glycoproteins, glycolipids, and/or a variety of carbohydrate epitopes. A number of these tumor antigens have been found to be up-regulated in the neoplastic disease state. Examples of tumor antigens that can signal a development and progression of a neoplastic disorder, and that can be detected by lectenz of the present invention, include, but are not limited to, carcinoembryonic antigen (CEA), which is a glycoprotein associated with colorectal, gastric, pancreatic, lung, and breast carcinomas, and the developing fetus; carbohydrate antigen 19-9 (CA 19-9), or sialylated Lewis A antigen, which is present in a glycolipid found in patients with pancreatic cancer; and carbohydrate antigen 15-3 (CA15-3), associated with breast cancer.

The presence of the antigen does not necessarily indicate transformation to a cancerous cell, however, its localization in the cell is indicative, as in the case of CEA. For this reason, there is a need for highly selective and high affinity analytical tools. The diagnostic tests currently rely on antibodies that were often generated against the peptide portions of the glycoprotein or sugar portions of glycolipid, however, the exact epitopes are only now being defined. In the examples in which the glycans have been characterized, multiple glycoforms are often present (CEA, for example). Lacking reagents that are able to discriminate between glycoforms, it is currently impossible to determine the extent to which subtle variations in glycosylation correlate with disease state, cancer type, or tissue localization. At present, these questions can be addressed primarily by MS analyses of isolated glycoproteins, which are examined as mixtures of glycoforms. Typically, the only level of glycoform-focusing that is performed is the enrichment in high-mannose containing glycans using lectin (concanavalin A, (Con A)) affinity chromatography. More efficient laboratory analyses and routine clinical diagnostic techniques remain severely limited by the lack of glycoform-specific reagents.

Lectenz of the present invention are particularly useful for quantifying the relative abundances of each glycoform present in any given glycoprotein in a biological sample. As used herein, the term "glycoform" refers to type of protein with a specific type of glycoprotein attached. Two proteins would be of the same glycoform if they carried the same glycoprotein. In some embodiments, lectenz of the present invention can be used to enrich the biological sample with a particular glycoform. In other embodiments, lectenz generated by the methods described herein can be used to identify specific glycosylation sites on the protein surface to which the glycans are attached. In these embodiments, lectenz specific for particular oligosaccharides will be used to separate intact glycopeptides from a proteolytic digest of any glycoprotein. For example, a PNGase-F derived lectenz can be used to separate N-linked glycopeptides from other glycopeptides or peptides, as might arise from a typical protease digestion of a glycoprotein. Enriching the sample in the analyte of interest is of great assistance in the further characterization of the glycopeptides fractions. In particular, enrichment facilitates the identification of the peptide sequence and the glycan structure, which can enable the identification within the intact protein of the glycosylation sites and the characterization of the particular glycans present at each glycosylation site.

In other embodiments, lectenz of the present invention will find their use in monitoring specific glycan modifications of proteins in biological fluids, tissues, organs, or living cells. Lectenz engineered by the method of the present invention will not depend on the identity of the protein, that is they will be context independent, and will be able to recognize any protein that comprises a given glycan, and therefore will be very useful for detection of given glycan modifications.

In yet other embodiments, lectenz of the present invention can be used for in vitro or in vivo staining cells or tissues.

In other embodiments, the lectenz can be developed so as to be specific for a particular glycoprotein or glycosylation site in a glycoprotein. Such a lectenz could be employed to monitor a particular glycoprotein in a mixture, as might arise during the production of recombinant glycoproteins for use in the pharmaceutical or research industries.

In the foregoing embodiments, the lectenz can be tagged with a stain or a dye and applied to a biological sample comprising cells or tissues or glycoproteins or glycopeptides or oligosaccharides or polysaccharides of interest.

In certain embodiments, lectenz of the present invention can be used as therapeutic agents. In these embodiments, design of a particular lectenz can based on glycosidases for which human homologues exist. This will ensure that such lectenz lack immune reactivity. In certain embodiments, lectenz of the present invention can be modified for delivery of an active therapeutic agent. Since lectenz of the present invention have a defined glycan specificity, a delivery of the therapeutic agents can be targeted only to those cells, tissues, or organs that display a particular glycan. Examples of therapeutic agent that can be used for site-specific delivery include, but are not limited to, various chemotherapeutic, antibiotic, and antiviral agents, toxins, radioisotopes, cytokines, etc.

In certain embodiments, lectenz of the present invention can be used as reagents for affinity separation, including, for example, affinity chromatography. Affinity chromatography is a method of separating biochemical mixtures, based on a highly specific biological interaction such as that between lectenz and glycan. The present invention is not limited to any specific design or chromatographic system. In general, lectenz will be either covalently attached or otherwise immobilized to the solid support, and will constitute a stationary phase. In certain embodiments, the lectenz-derivativized stationary phase can be used in column chromatography. In these embodiments, the particles of the solid stationary phase will be used to fill the whole inside volume of the tube (packed column). Alternatively, the solid phase particles will be concentrated on or along the inside tube wall leaving an open, unrestricted path for a biological sample (i.e., the mobile phase) in the middle part of the tube (open tubular column). In other embodiments, the lectenz-derivativized stationary phase can be used for batch chromatography. In these embodiments, the stationary phase can be added to a vessel and mixed with the biological sample. Although the foregoing example generally focused on affinity chromatography, it is understood that these principals are readily applied to other affinity purification protocols.

EXAMPLES

Example 1

Target Enzymes for Conversion to Lectenz

Target Enzymes for Conversion to Carbohydrate-Biosensors (Lectenz)

Presented in Table 1 are three initial glycosidases that can be subjected to redesign as lectenz. Lectenz 1 will find broad use in all aspects of glycomics analysis. Lectenz 2 will be vital to furthering the analysis of glycans in diabetes, and lectenz 3 will be useful in characterizing human versus avian influenza receptors.

Moreover, glycomics sequencing is focused on the analysis of trypsin-produced glycopeptides in order to map particular N-linked glycan structures to each glycosylation site

TABLE 1

Initial target enzymes for conversion to carbohydrate-biosensors (Lectenz)

| Lectenz ID | Enzyme | Specificity | Source/ Recombinant Expression Vector | Available Structure |
|---|---|---|---|---|
| 1 | PNGase F, Peptide-N4-(acetyl-β-D-glucosaminyl)-asparagine amidase | N-linked oligosaccharides(a)[ | F. meningosepticum/ E. coli | X-ray (b) |
| 2 | β-O-GlcNAcase, N-acetyl-β-D-glucosaminidase | O-linked β-GlcNAc, monosaccharide(c) | B. thetaiotaomicron/ E. coli | X-ray (d) |
| 3 | Neuraminidase, N-acetyl-neuraminate glycohydrolase | Terminal non-branched α-(2,3) and α-(2,6)-Neu5Ac(e) | C. perfringens/ E. coli | Comparative model (f) |
| | | Additional Targets | | |
| 4 | α-(1-2)-Mannosidase | α-(1-2)-Man on High mannose N-glycans | Human, mouse, S. cerevisiae/ P. pastoris | X-ray (g) |
| 5 | α-Galactosidase | α-Gal on glycoproteins and glycolipids | Human/ human cells | X-ray (h) |
| 6 | β-Galactosidase | β-Gal on glycoproteins and glycolipids | E. coli/E. coli | X-ray (i) |
| 7 | α-1,2/3/6-Mannosidase | α-1,2/3/6 Man on High mannose N-glycans | Human, mouse/ P. pastoris | X-ray (j) |

(a) Haslam et al., Core fucosylation of honeybee venom phospholipase A2. Glycobiology, 1994. 4(2): p. 105-6.
(b) Kuhn et al., Crystal-Structure of Peptide-N-4-(N-Acetyl-Beta-D-Glucosaminyl) Asparagine Amidase-F at 2.2-Angstrom Resolution. Biochemistry, 1994. 33(39): p. 11699-11706.
(c) Gao et al., Dynamic O-glycosylation of nuclear and cytosolic proteins: cloning and characterization of a neutral, cytosolic beta-N-acetylglucosaminidase from human brain. J Biol Chem, 2001. 276(13): p. 9838-45.
(d) Dennis et al., Structure and mechanism of a bacterial beta-glucosaminidase having O-GlcNAcase activity. Nat. Struct. Mol. Biol., 2006. 13(4): p. 365-71.
(e) Mizan et al., Cloning and characterization of sialidases with 2-6' and 2-3' sialyl lactose specificity from Pasteurella multocida. J. Bacteriol., 2000. 182(24): p. 6874-83.
(f) Pieper et al., MODBASE, a database of annotated comparative protein structure models, and associated resources. Nucleic Acids Res, 2004. 32(Database issue): p. D217-22.
(g) Tempel et al., Structure of Mouse Golgi a-Mannosidase IA Reveals the Molecular Basis for Substrate Specificity among Class 1 (Family 47 Glycosylhydrolase) a1,2-Mannosidases. J. Biol. Chem., 2004. 279(28): p. 29774-29786.
(h) Garman and Garboczi, The molecular defect leading to Fabry disease: structure of human alpha-galactosidase. J Mol Biol, 2004. 337(2): p. 319-35.
(i) Jacobson et al., Three-dimensional structure of beta-galactosidase from E. coli. Nature, 1994. 369(6483): p. 761-6.
(j) Heikinheimo et al., The structure of bovine lysosomal alpha-mannosidase suggests a novel mechanism for low-pH activation. J Mol Biol, 2003. 327(3): p. 631-44.
Lectenz 1: Glycomics Affinity Reagent for Enrichment of N-linked Glycans (specific for N-linked oligosaccharides not containing core fucose)

In many applications, particularly those that involve analysis of clinical tissue and fluids, there is great interest in identifying changes in protein and glycoprotein expression as a function of disease progression. If changes in the expression of specific molecules can be highly correlated with disease state, then they can be exploited to develop potential diagnostics and, perhaps, reagents to image diseased cells and tissues. A difficulty that underlies all of these analyses is because these mixtures are so complex, it is extremely challenging to develop separation methods that allow subsequent identification and quantification of the majority of individual species present in a sample using mass spectrometry. Furthermore, convincing evidence demonstrates that changes in the glycans expressed on proteins can serve as additional markers for disease. There is a great need, therefore, to be able to rapidly separate proteins from glycoproteins and peptides from glycopeptides to enable identification and quantification for correlation with disease states. In serum, for example, half of the components are estimated to be non-glycosylated, with albumin by far the most abundant. If these proteins could be separated from the glycoproteins, then the complexity falls by a factor of 2.

on each peptide. In this type of analysis, the majority of species produced by the proteolytic digest by far are non-glycosylated peptides. The ability to separate these from the glycopeptides of interest would greatly simplify the analysis to yield site-specific glycan information. The choice of PNGase F for the scaffold is based on the fact that this enzyme is widely used to remove N-glycans from glycoproteins and glycopeptides for further analysis. It is robust, and its action is universal, as long as peptides do not contain core α-1-3 fucosylation, which is not expressed in vertebrates. Further, it is fully active on species that express the α-1-6 fucosylation, such as vertebrates. The PNGase F lectenz would be extremely useful for separating glycoproteins and glycopeptides from extracts, fluids, and even purified glycoproteins for further detailed structural analysis by mass spectrometry. This reagent could be used to extract the needle (glycopeptides) from the haystack (proteolytic peptides) in a proteomics/glycomics analysis.

The initial PNGase lectenz scaffold will be generated from the enzyme produced by Flavobacterium meningosepticum, for which a crystal structure has been reported in complex with substrate. The presence of a crystal structure is significant for the computational optimization of lectenz-glycan affinity. In addition, preliminary point mutagenesis studies have identified a single mutation (D60N) that renders PNGase F completely inactive.

Lectenz 2: Biosensor for Diabetes-Related Protein Hyper-GlcNacylation (Specific for βO-GlcNAc)

A neutral, nucleocytoplasmic hexosaminidase was first described in 1975 and characterized as O-GlcNAcase in 1994. It has only recently been cloned (by Dr. L. Wells at the CCRC) and identified as a nucleocytoplasmic, neutral β-N-acetylglucosaminidase (O-GlcNAcase, OGA, EC 3.2.1.52). Unlike hexosaminidase A or B, OGA is localized to the cytosol and to a lesser degree the nucleus, has a neutral pH optimum, and does not catalyze the removal of nor is inhibited by GalNAc. The role of O-GlcNAcase in apoptosis has yet to be elucidated; however, cleavage of the enzyme near the middle of the polypeptide has no effect on enzyme activity, suggesting that the N-terminal "hyaluronidase-like" domain is sufficient for activity. Very recently crystal structures of O-GlcNAcase from *Clostridium perfringens*, both free and complexed with inhibitors, have been reported. They have high homology with the human protein and provide an excellent basis for computational studies.

Lectenz 3: Biosensor for the Human Influenza Receptors α-2,6-Linked Neuraminic Acid (Specific for α-Neu5Ac-(2,6)-β-Gal)

The human cell-surface carbohydrate (neuraminic or sialic acid) targeted by the hemagglutinin protein of influenza virus. Hemagglutinin mediates attachment to and entry of the virus into host cells by binding to sialic acid receptors at the cell surface. Human influenza viruses preferentially bind to sialic acid linked to galactose by α-2,6 linkages; the main type found on the epithelial cells of the human upper respiratory tract. Avian viruses tend to bind to α-2,3 linkages that are found on avian intestinal epithelium and, to a lesser extent, the lower human respiratory tract. Thus, this receptor is a key determinant of host specificity and an important target for potential prevention and treatment of influenza. Our initial lectenz scaffold will be the 2,6-sialidase nanB, isolated from *P. multocida*, cloned and expressed in *E. coli* by colleagues at UGA (Dr. M. Lee, J Bacteriol. 2000 December; 182(24): 6874-6883.) This is so far the only neuraminidase that has a marked preference for the human 2-6 linkage. A 3D structure (Q27701) for this enzyme has been generated by comparative modeling, from PDB template 2SLI (a hydrolase in the same family) and deposited in the Modbase database, which will serve as a basis for the computational analysis. The ligand can be docked into the presumed active site using AutoDock with the GLYCAM parameters. Concurrently, characterization of the structure can occur experimentally using protein crystallography, NMR spectroscopy, and site-directed mutagenesis.

MD Simulation of the PNGase F—Chitobiose Complex

A 5 ns fully solvated MD simulation of the PNGase F—chitobiose complex was performed under nPT conditions (300 K, 1 atm) employing the AMBER/GLYCAM protein/carbohydrate force field and the experimental X-ray structure for the complex. Prior to energy analysis, the root mean squared difference (RMSD) in the positions of the Cα atoms was determined as a function of the simulation time (FIG. 3) to determine the stability of the simulation and the level of conformational equilibration. On the basis of that data, it was determined that the average RMSD (1.5 A) was reasonable; however, the simulation was slow to equilibrate. Consequently, the first 1 ns of data were not included in subsequent analyses.

Ligand stability in the binding site was assessed by monitoring intermolecular hydrogen bonds between the chitobiose and the protein (FIG. 4). Average values for the hydrogen bonds and their percentage occupancies are presented in Table 2 along with the crystallographically determined values.

TABLE 2

Selected hydrogen bond lengths and occupancies computed between chitobiose and PNGase F

| Hydrogen bonds | X-ray (b) | Average from MD Simulation | Occupancy |
|---|---|---|---|
| D60-Oδ - GlcNAc316 O1 | 3.02 | 2.76 ± 0.1 | 100% |
| D60-O - GlcNAc316 NAc | 2.97 | 2.84 ± 0.1 | 100% |
| R61-NH - GlcNAc317 OAc | 2.84 | 2.91 ± 0.1 | 93% |
| R61-NH - GlcNAc316-O4 | 2.92 | 2.90 ± 0.1 | 93% |
| R61-NH2 - GlcNAc317 OAc | 3.03 | 2.90 ± 0.1 | 76% |
| W120-Nε - GlcNAc317-O6 | 2.93 | 2.98 ± 0.1 | 39% |
| W191-Nε - GlcNAc316-O3 | 2.96 | 3.06 ± 0.1 | 10% |
| E118-Oε - GlcNAc317-O6 | 3.25 | —[a] | |

[a]Occupancies determined using a standard 3.3 Å cutoff.

[b]Kuhn et al., Crystal-Structure of Peptide-N-4-(N-Acetyl-Beta-D-Glucosaminyl) Asparagine Amidase-F at 2.2-Angstrom Resolution. Biochemistry, 1994. 33(39): p. 11699-11706.

Having confirmed that the MD simulation is stable and able to reproduce the experimental interactions between the ligand and the protein, it was then employed in subsequent binding energy and alanine scanning analyses.

Identification of Hotspots and Key Residues by Interaction Energy Analysis

We employed the generalized Born (GB) continuum solvent model as implemented in AMBER, with solvent parameters developed for protein-ligand interactions. We have previously reported that these solvent parameters perform well for carbohydrate-antibody and carbohydrate-lectin MM-GB binding energy predictions. The contributions to the binding energy were computed for the 313 amino acids in PNGase F. The interaction energies are presented in Table 3 for all residues that are within 4.5 Å of the ligand (within a contact zone), as well as for any others that contributed at least less than −0.5 kcal/mol to either the total MM (van der Waals and electrostatic) interaction energy ($\Delta E_{MM}$) or the total binding free energy ($\Delta G_{Binding}$). Also included are any residues that contributed unfavorably to substrate binding, such as D60 and E206.

The total interaction energy (−13.7 kcal/mol) is comparable to data computed for the similar size galectin-1—LacNAc complex, and as in the case of galectin-1, overestimates the experimental affinity due to the omission of conformational and configurational entropy. Nevertheless, the per-residue interaction energies can be used to identify key amino acid residues. The majority of the per-residue net binding energies were favorable, with the notable exceptions of D60 and E206 (FIG. 5). D60 is the primary catalytic residue, while E206 and E118 are thought to be important for stabilization of reaction intermediates. Thus, it is significant, but perhaps not surprising, that these two residues were identified as the most destabilizing to the disaccharide product of the hydrolysis reaction.

A possibly unfavorable interaction was also exhibited by D57, which has an unfavorable $\Delta E_{mm}$ that is offset by a negative solvation free energy $\Delta G_{GB}$. As has been observed for the galectin-1—LacNAc complex, the quasi-enthalpic contributions ($\Delta E_{mm}$) and the entropy-related desolvation $\Delta G_{GB}$ terms are often similar in magnitude and opposite in sign, making the selection of the solvation model critical. In general, all such potentially key sites are included in the display library, rather than rely exclusively on the accuracy of the theoretical computations.

Figure 5:
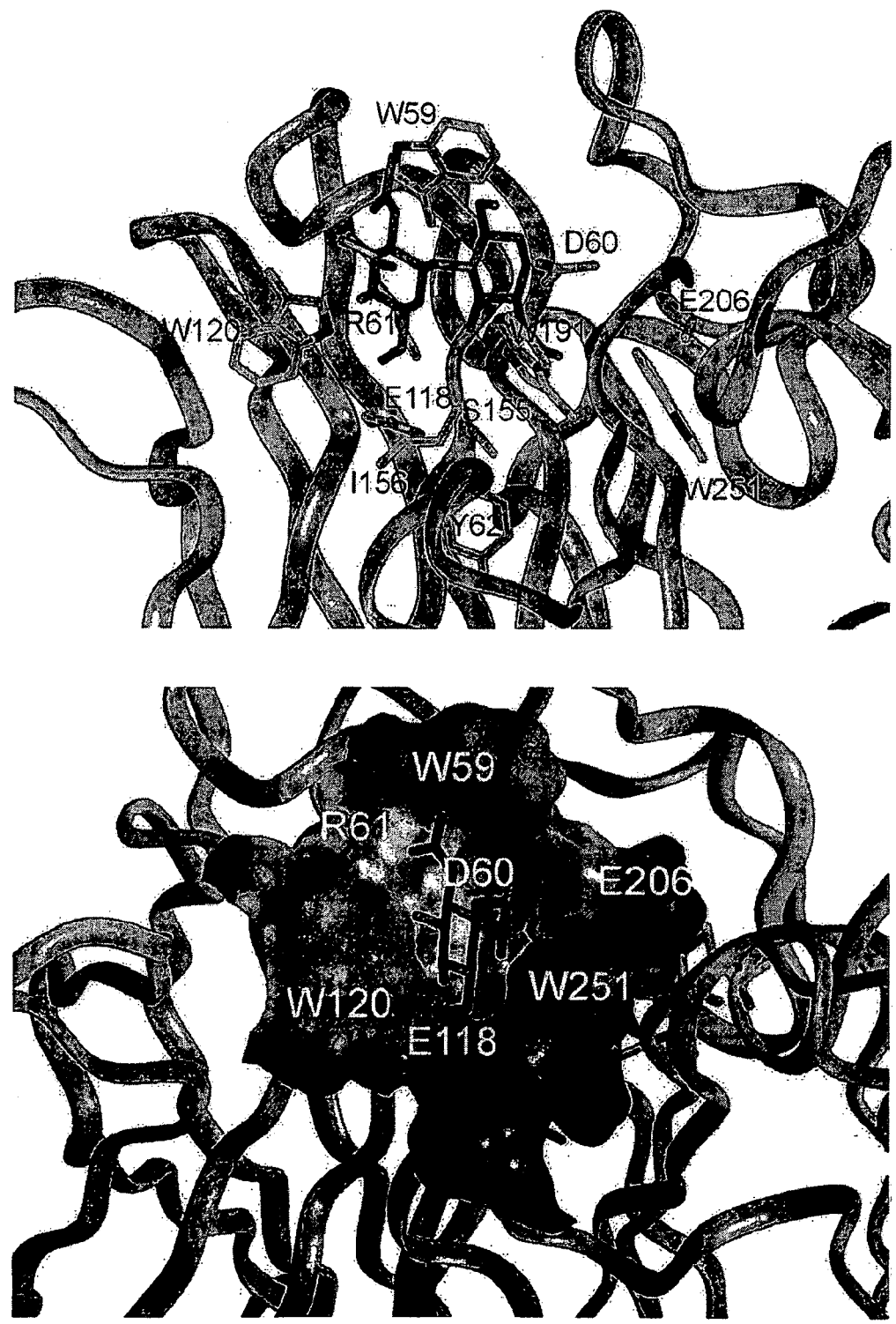
FIG. 5 depicts, in the left image: residues within 4.5 Å of the disaccharide ligand (dark grey) in the binding site of PNGase F. In the right image: the solvent accessible surface with the residues identified as most significant for binding labeled.

FIG. 5. represents, in the left image: residues within 4.5 Å of the disaccharide ligand (red) in the binding site of PNGase F. In the right image: the solvent accessible surface with the residues identified as most significant for binding labeled.

Direct comparisons with the data in Table 4 are possible with two similar carbohydrate-protein complexes (galectin-1—LacNAc and Con A—trimannoside), both of which employed the AMBER/GLYCAM force field and the GB solvation approximation. In Table 3, as in the MM-GB analysis of galectin-1 and Con A, the majority of the molecular mechanical energy (−33.8 kcal/mol) arises from electrostatic interactions (−20.8). However, both the van der Waals and the electrostatic contributions (−12.9 kcal/mol and −20.8 kcal/mol, respectively) are lower than those observed for related disaccharides bound to galectin-1 (—17 to −24 kcal/mol for van der Waals and −30.8 to −67.5 kcal/mol for electrostatics), strongly suggesting that there is room for affinity enhancement via side chain optimization in PNGase F. Further, it can be seen that electrostatic contribution is approximately cancelled by desolvation free energy. This phenomenon has been observed in both previous studies and can be a manifestation of entropy-enthalpy compensation. An advantage can therefore arise from cancellation of errors in the GB calculation.

On the basis of the energies in Table 3, the known inactive D60A mutant was generated and the energies recomputed. The binding energy markedly improved in the D60A mutation (total $\Delta E_{MM}$=−35.5, $\Delta G_{GB}$=19.6, and $\Delta G_{Binding}$=−15.9, see Table 5) for a net gain in affinity of approximately 2 kcal/mol.

TABLE 3

Residue contributions (kcal/mol) to the binding free energy for wild type PNGase F bound to substrate, chitobiose (β-GlcNAc-(1,4)-β-GlcNAc-OH)

| Contact Zone Residues | $\Delta E_{VDW}$ | $\Delta E_{ELE}$ | $\Delta E_{MM}$ | $\Delta G_{GB}$ | $\Delta G_{Binding}$ |
|---|---|---|---|---|---|
| R61 | −1.5 | −15.1 | −16.7 | 12.3 | −4.4 |
| W120 | −3.1 | −2.3 | −5.4 | 1.9 | −3.5 |
| D60 (nucleophile in enzyme) | −0.9 | −3.9 | −4.8 | 5.2 | 0.4 |
| W59 | −3.1 | −0.2 | −3.3 | 0.3 | −3.0 |
| W191 | −1.3 | −1.6 | −2.9 | 1.3 | −1.6 |
| W251 | −0.7 | −0.3 | −1.0 | 0.1 | −0.9 |
| Y62 | −0.6 | −0.1 | −0.6 | 0.0 | −0.6 |
| E118 | −0.5 | −0.1 | −0.5 | 0.6 | 0.1 |
| I156 | −0.2 | 0.1 | −0.2 | −0.1 | −0.3 |
| S155 | −0.3 | 0.2 | −0.1 | −0.1 | −0.1 |
| G192 | 0.0 | 0.1 | 0.0 | 0.0 | 0.0 |
| E206 | −0.3 | 2.1 | 1.8 | −1.1 | 0.7 |
| Other potentially important residues identified from 313 total residues ($|\Delta E_{MM}|$ or $|\Delta G_{Binding}| \geq 0.5$) |  |  | $\Delta E_{MM}$ | $\Delta G_{GB}$ | $E_{Total}$ |
| T119 | −0.2 | −0.6 | −0.7 | 0.8 | 0.1 |
| R248 | −0.1 | −1.2 | −1.4 | 1.2 | −0.1 |
| K123 | 0.0 | −0.5 | −0.5 | 0.6 | 0.1 |
| R125 | 0.0 | −0.4 | −0.4 | 0.6 | 0.1 |
| D57 | −0.1 | 3.0 | 2.9 | −3.5 | −0.6 |
| Total Binding Energy $\Delta G_{Binding}$ | −12.9 | −20.8 | −33.8 | 20.1 | −13.6 |

TABLE 4

Total interaction energies (kcal/mol) for favorable mutants identified by alanine and electrostatic scanning of PNGase F bound to chitobiose

| Contact Zone Residues | $\Delta E_{MM}$ | $\Delta G_{GB}$ | $\Delta G_{Binding}$ |
|---|---|---|---|
| Wild type enzyme (D60) | −37.1 | 23.5 | −13.7 |
| D60A | −35.5 | 19.6 | −15.9 |
| E206A | −40.7 | 23.6 | −17.2 |
| D60A/E206A | −37.2 | 21.0 | −16.4 |

Subsequently, alanine scanning was performed on the D60A mutant to look for possible further key residues (Table 5). One double mutant was subsequently identified (D60A/E206A) with any enhanced affinity (−0.5 kcal/mol), while five residues were confirmed as being critical to ligand binding (W251, W191, W120, W59, and R61).

TABLE 5

Relative[a] interaction energies (kcal/mol) predicted from alanine scanning for the D60N mutant of PNGase F bound to chitobiose

| Mutation | $\Delta\Delta E_{MM}$ | $\Delta\Delta G_{GB}$ | $\Delta\Delta G_{Binding}$ |
|---|---|---|---|
| D60A | 1.8 | −4.0 | −2.2 |
| E206A | −1.9 | 1.2 | −0.7 |
| D60A/E206A[b] | −1.9 | 1.4 | −0.5 |
| D60A/S155A | −0.1 | 0.0 | −0.1 |
| D60A/I82A | 0.3 | 0.1 | 0.4 |
| D60A/Y62A | 0.1 | 0.0 | 0.1 |
| D60A/I156A | 0.1 | 0.1 | 0.2 |
| D60A/E118A | −0.2 | 0.2 | 0.0 |
| D60A/W251A | 1.0 | 0.0 | 1.0 |
| D60A/W191A | 2.6 | −1.0 | 1.5 |
| D60A/W59A | 3.0 | −0.4 | 2.6 |
| D60A/W120A | 5.1 | −2.1 | 3.0 |
| D60A/R61A | 15.5 | −11.7 | 3.8 |

[a]Relative to wild type sequence (D60).
[b]Double mutants are relative to initial mutant (D60A).

Rather than performing side chain repacking experiments initially, scanning the inactive mutant for positions that could lead to favorable electrostatic interactions was performed. This scanning was performed with both theoretical positive and negative probe residues (see experimental design) over all of the residues in the immediate contact zone (Table 6).

Although no mutations to charged residues were predicted to lead to enhanced total binding energies, several possible mutations were suggested to lead to improved molecular mechanical interactions. Thus, residues E206, 5155, E118, and Y62 can each be mutated to Arg and Lys and the energies recomputed. The resulting binding free energies can be used to select any further specific point mutants to clone and over-express. This perhaps is not surprising given that carbohydrate-protein interactions are characterized by an intricate network of hydrogen bonds, and perturbations of that network might rarely be favorable. It is again significant that E206 and E118, which have both been implicated in the enzyme mechanism, have been identified as potential key residues for affinity optimization. It is also notable for the design of the display library that no mutations to negatively charged residues were predicted to lead to improved affinities.

TABLE 6

Interaction energies relative to D60A mutant for key residues predicted from electrostatic alanine scanning.

| Contact Zone Residue | $\Delta\Delta E_{MM}$ | ALA+ $\Delta\Delta G_{GB}$ | $\Delta\Delta G_{Binding}$ |
|---|---|---|---|
| E206A+ | −3.5 | 3.7 | 0.2 |
| S155A+ | −1.0 | 2.7 | 1.6 |
| E118A+ | −0.7 | 2.9 | 2.1 |
| Y62A+ | −0.4 | 4.2 | 3.8 |

Based on the computational affinity data, several mutants were selected for cloning and have been over-expressed in E. coli. The results of experimental affinity analyses are presented in the following section.

Experimental Binding Affinity Measurements for PNGase F Lectenz

Presented in Table 7 are the dissociation constants measured using surface Plasmon resonance (SPR) for the interaction between denatured RNase B, which contains a single N-glycosylation site predominantly occupied by high mannose oligosaccharides and mutants of PNGase F.

TABLE 7

Dissociation constants measured for the interaction between denatured glycoprotein RNase B and lectenz mutants of PNGase F.

| Lectenz | $K_d$ | Relative[c] Enhancement | Lectenz | Relative[c] Enhancement | $K_d$ |
|---|---|---|---|---|---|
| D60 (wild type)[a] | $6.4 \times 10^{-3}$ | 1 | D60A/E206K | 360 | $1.8 \times 10^{-5}$ |
| D60A | $1.1 \times 10^{-5}$ | 580 | D60A/R125A | 360 | $1.8 \times 10^{-5}$ |
| D60N[b] | $2.1 \times 10^{-5}$ | 290 | D60A/E206R | 240 | $2.7 \times 10^{-5}$ |
| E206A | $1.1 \times 10^{-5}$ | 580 | D60A/E206Q | 360 | $1.8 \times 10^{-5}$ |
| D60A/E206A | $2.0 \times 10^{-5}$ | 320 | D60A/D57A | 910 | $7.0 \times 10^{-6}$ |

[a]$K_m$.
[b]Reported inactive mutant.
[c]Relative to wild type.

As predicted computationally, both the E206A and D60A mutants have markedly enhanced binding. Also, as suggested from electrostatic scanning, a positive charge (K or R) at E206 provides a modest further increase in affinity. At present, without the benefit of side chain repacking experiments or saturation mutagenesis, the first generation lectenz has micromolar affinity and with only two point mutations, has reached the micromolar level. It is worth noting that these preliminary mutations have enhanced the affinity of the PNGase lectenz nearly to that exhibited by the lectin Con A for high mannose oligosaccharides ($K_d \approx 1 \times 10^{-6}$ M).

As mentioned in section B, high affinity is only one desirable property for a biosensor. High affinity will permit the reagent to be employed in affinity chromatography. However, it is also important to achieve a slow off-rate ($k_{off}$) if the biosensor is to be used successfully in such applications as tissue staining.

Figure 6:
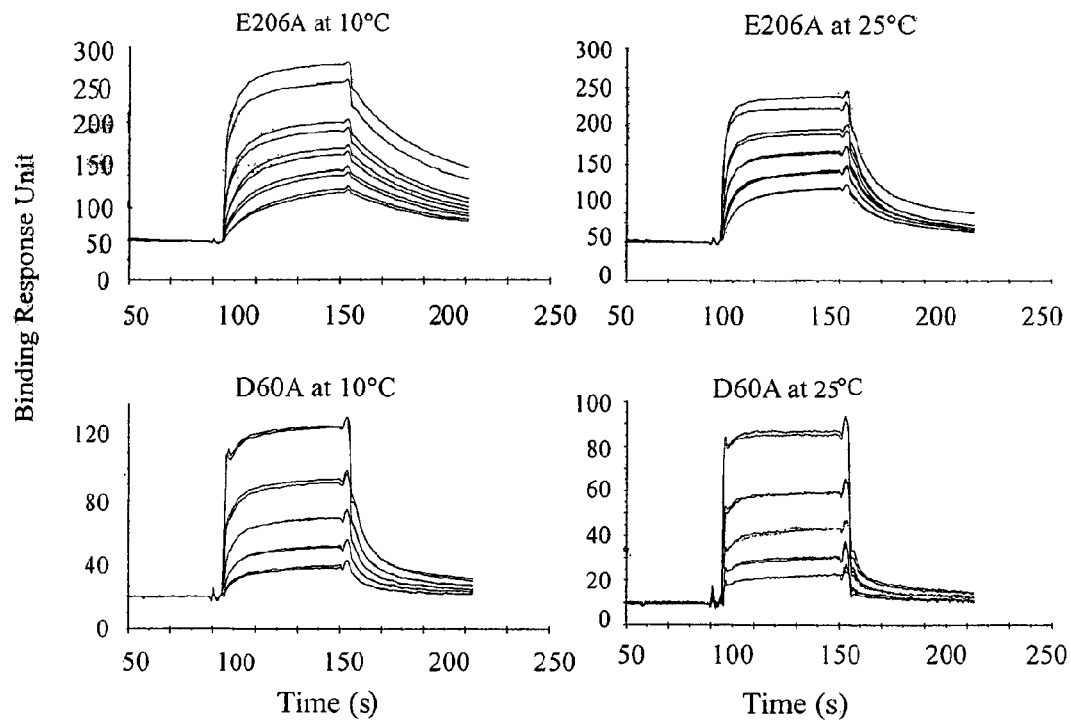
FIG. 6 depicts SPR sensograms indicating the variations in kinetic on- and off-rates as a function of mutation and temperature (10° C. and 25° C.).
Figure 6:
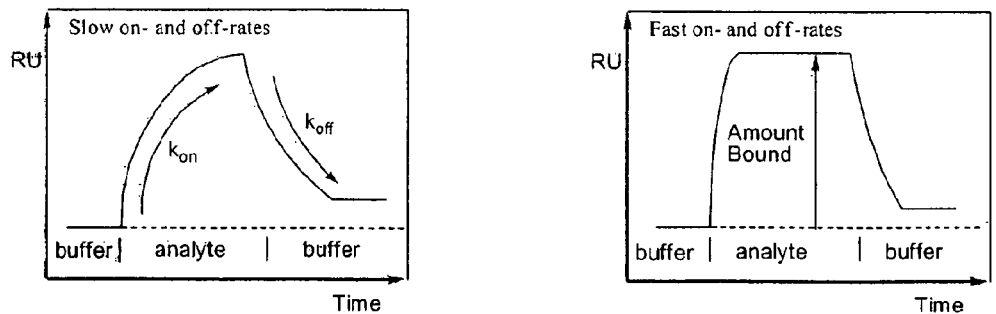

SPR provides a convenient method for assessing variations in $k_{off}$. An examination of FIG. 6 indicates significantly different kinetic behavior between mutants D60A and E206A. Both mutants have similar values for $K_d$ (Table 7), but D60A displays rapid on and off rates (at both 10 and 25° C.), while E206A presents substantially decreased off-rates at both temperatures. This is an extremely significant feature as it suggests that the kinetics of binding will be tunable to achieve a range of properties.

Further Affinity Enhancement

On the basis of the computational data, a focused yeast display library for the inactive D60A mutant containing the following 7 residues: D57, Y62, E118, S155, I156, G192, and E206 was developed. These 7 positions were randomized to all 20 amino acids, resulting in a theoretical diversity of $20^7$ ($\approx 10^9$) clones at the amino acid level.

In addition, computational side chain repacking experiments on a subset of the same residues Y62, E118, I156, S155, G192, E206, and D57 employing the D60A mutant can be performed. By performing computational mutagenesis on the same set of key residues, we expect to be able to discover the extent to which the computational analysis is able to reproduce the optimized mutagenesis data. The effects of modifications of the computational method (such as implicit solvation model) so as to enhance its accuracy can be performed.

Example 2

Directed Evolution of Lectenz

A DNA library was created based on the inactive D60A mutant of the PNGase F enzyme. The residues D57, Y62, E118, S155, I156, G192, and E206 identified from computational analysis were randomized at the DNA level to encode for all twenty amino acids. The library was cloned into the yeast display vector pPNL6 and transformed into yeast.

The library was panned against dRNAse B captured on magnetic beads for two rounds then sorted for c-myc positive yeast by flow cytometry in the third round. The three rounds were repeated once for a total of six rounds. Table 8 shows the enrichment of yeast clones by sequencing the DNA of 18 clones from round six.

TABLE 8

Enrichment of clones from round six.

| Round 6 Clones | Clone Enrichment |
|---|---|
| R6.1.7 | 3/18 |
| R6.1.12 | 4/18 |
| R6.1.13 | 3/18 |

Clone R6.1.13 was selected for functional analysis using a competition assay and was expressed in bacteria and purified. In the assay, 50 µL of a 1 µM solution of R6.1.13 was preincubated with dRNAse B beads. Similarly, 50 µL of a 1 µM solution of the inactive enzyme D60A mutant was preincubated with dRNAse B beads. To each pre-incubated solution, Con A lectin (fluorescently labeled with DyLight 488) was added to a final concentration of 100 nM. Labeled Con A was also added to beads with and without dRNAse B as controls to a final concentration of 100 nM. The fluorescence of the beads was measured by flow cytometry. The fraction of Con A bound was normalized to the fluorescence of beads with and without dRNAse B (see FIG. 9).

Clone R6.1.13 protein showed approximately a 36% increased inhibition of Con A binding to dRNase beads, compared to the inactive enzyme D60A mutant, indicating affinity enhancement. This clone has not been fully optimized, as indicated by the modest clone enrichment of 3/18 (Table 8), and so further affinity improvements can be obtained by further rounds of enrichment.

What is claimed is:

1. A method for generating a lectenz comprising an inactivated mutated carbohydrate-processing enzyme having enhanced affinity for its substrate compared to a corresponding wild-type carbohydrate-processing enzyme, the method comprising:
   (a) providing a 3D structure of an enzyme-substrate complex comprising a substrate bound to a catalytically inactive mutant carbohydrate-processing enzyme or a corresponding wild-type carbohydrate-processing enzyme, wherein the catalytically inactive carbohydrate-processing enzyme comprises an amino acid sequence comprising at least one inactivating mutation that eliminates catalytic activity of the enzyme;
   (b) performing a computational simulation on the enzyme-substrate complex to predict the per-residue contributions to total interaction energy ($\Delta E_{MM}$) and/or total binding free energy ($\Delta G_{Binding}$) for amino acid residues of the enzyme;
   (c) analyzing the per-residue energetic contributions to identify at least one amino acid residue as a potential mutation site for enhancing binding affinity of the inactivated enzyme for its substrate as compared to a wild-type enzyme, wherein an amino acid residue is identified as a potential mutation site for enhancing binding activity when
      (i) for an amino acid residue located within 5 Å of the substrate in the enzyme-substrate complex, the per-residue contribution of the amino acid residue to at least one of $\Delta E_{MM}$ or $\Delta G_{Binding}$ is ≥–0.7 kcal/mol; and
      (ii) for an amino acid residue located more than 5 Å from the substrate in the enzyme-substrate complex, the per-residue contribution of the amino acid residue to at least one of $\Delta E_{MM}$ or $\Delta G_{Binding}$ is ≥0.0 kcal/mol;

(d) expressing a library of inactivated mutated carbohydrate-processing enzymes, each inactivated mutated enzyme comprising a plurality of amino acid mutations, wherein each inactivated mutated enzyme comprises at least one inactivating mutation that eliminates catalytic activity of the enzyme; and each inactivated mutated enzyme further independently comprises at least one potential affinity-enhancing mutation at a site identified in step (c);

(e) assaying the inactivated mutated enzymes of step (d) for their ability to form the enzyme-substrate complex; and (f) identifying inactivated mutated enzymes from step (e) that exhibit binding affinities to the substrate that are at least 1.2-fold greater than those of the wild-type carbohydrate-processing enzyme.

2. The method of claim 1, wherein at least one potential affinity-enhancing mutation is an amino acid substitution that replaces an amino acid residue located within 5 Å of the substrate when bound to the wild-type or inactivated enzyme.

3. The method of claim 2, wherein at least one amino acid being replaced makes a favorable (<0.0 kcal/mol) per-residue contribution to the total interaction energy ($\Delta E_{MM}$) or total binding free energy ($\Delta G_{Binding}$).

4. The method of claim 3, wherein the per-residue contribution of the amino acid being replaced is between −0.5 kcal/mol and 0.0 kcal/mol.

5. The method of claim 1, wherein at least one potential affinity-enhancing mutation is an amino acid substitution that replaces an amino acid that makes an unfavorable (>0.0 kcal/mol) per-residue contribution to the total interaction energy ($\Delta E_{MM}$) or total binding free energy ($\Delta G_{Binding}$).

6. The method of claim 1, wherein at least one of step (b) or step (c) comprises computational alanine scanning mutagenesis, direct ΔG calculations, or thermodynamic integration calculations.

7. The method of claim 1, wherein the simulation comprises molecular dynamics simulation, Monte Carlo simulation, or side-chain rotamer searching.

8. The method of claim 1, wherein the simulation is performed using classical force fields.

9. The method of claim 1, wherein the library of step (d) comprises inactivated mutated enzymes comprising the same inactivating mutation.

10. The method of claim 1, wherein the library of step (d) comprises inactivated mutated enzymes comprising different inactivating mutations.

11. The method of claim 1, wherein the library is a randomized library.

12. The method of claim 1, wherein the 3D structure of the enzyme-substrate complex is an X-ray structure.

13. The method of claim 12, wherein the X-ray structure represents an inactive enzyme-substrate complex, an active enzyme-inhibitor complex, or an enzyme-product complex.

14. The method of claim 1, further comprising generating the 3D structure using homology or comparative modeling.

15. The method of claim 1, further comprising generating the 3D structure from crystallographic data from a free enzyme by predicting a co-complex with a substrate using a computational docking program.

16. The method of claim 1, wherein the carbohydrate-processing enzyme is PNGaseF, and wherein the inactivated mutated carbohydrate-processing enzymes of step (d) comprise amino acid mutations at D57, Y62, E118, S155, 1156, G192 and E206.

17. A method for generating a novel biomolecule, wherein the biomolecule comprises a carbohydrate-binding protein having one or more mutations that:

(i) increase the affinity of the protein to its carbohydrate ligand, as compared to a wild-type protein; and (ii) have substantially no alteration in the specificity of the protein;

the method comprising:

(a) performing a computational simulation on the carbohydrate-protein complex to predict per-residue contributions to total interaction energy ($\Delta E_{MM}$) or total binding free energy ($\Delta G_{Binding}$) for amino acid residues of the protein;

(b) analyzing the per-residue energetic contributions to identify at least one amino acid residue as a potential mutation site for enhancing binding affinity of the protein for the carbohydrate ligand as compared to a wild-type protein, wherein an amino acid residue is identified as a potential mutation site for enhancing binding affinity when the amino acid residue is located within 5 Å of the carbohydrate ligand in the carbohydrate-protein complex, and the per-residue contribution of the amino acid residue to at least one of $\Delta E_{MM}$ or $\Delta G_{Binding}$ is ≥−0.7 kcal/mol;

(c) expressing a library of mutant carbohydrate-binding proteins, wherein each mutant carbohydrate-binding protein independently comprises at least one potential affinity-enhancing amino acid substitution that replaces an amino acid residue identified in step (b);

(d) assaying the mutant proteins of step (c) for their ability to form the carbohydrate-protein complex and for binding specificity; and
(e) identifying mutant proteins from step (d) that exhibit binding affinities to the carbohydrate that are at least 1.2-fold greater than those of wild-type protein.

18. The method of claim 17, wherein the biomolecule is a lectin or an antibody.

* * * * *

UNITED STATES PATENT AND TRADEMARK OFFICE
CERTIFICATE OF CORRECTION

PATENT NO. : 9,926,612 B2  
APPLICATION NO. : 13/148289  
DATED : March 27, 2018  
INVENTOR(S) : Woods et al.

Page 1 of 1

It is certified that error appears in the above-identified patent and that said Letters Patent is hereby corrected as shown below:

In the Specification

Column 28, Line 9: '1156' should read --I156--

In the Claims

Column 30, Line 35: '1156' should read --I156--

Signed and Sealed this  
Thirteenth Day of November, 2018

Andrei Iancu  
*Director of the United States Patent and Trademark Office*

UNITED STATES PATENT AND TRADEMARK OFFICE
CERTIFICATE OF CORRECTION

PATENT NO. : 9,926,612 B2
APPLICATION NO. : 13/148289
DATED : March 27, 2018
INVENTOR(S) : Robert J. Woods and Loretta Yang Page 1 of 1

It is certified that error appears in the above-identified patent and that said Letters Patent is hereby corrected as shown below:

In the Specification

Column 1, Line 12, 'Part of the work performed during development of this invention utilized U.S. Government funds under R41GM086991 awarded by the National Institutes of Health. Therefore, the U.S. Government has certain rights in this invention.' should read --This invention was made with government support under GM086991 awarded by the National Institutes of Health. The government has certain rights in the invention.--

Signed and Sealed this
Tenth Day of December, 2024

Katherine Kelly Vidal
*Director of the United States Patent and Trademark Office*